US010569088B2

(12) United States Patent
Dinsmoor et al.

(10) Patent No.: US 10,569,088 B2
(45) Date of Patent: Feb. 25, 2020

(54) DORSAL SPINAL COLUMN CHARACTERIZATION WITH EVOKED POTENTIALS

(71) Applicant: Medtronic, Inc., Minneapolis, MN (US)

(72) Inventors: David A. Dinsmoor, North Oaks, MN (US); Timothy J. Denison, Minneapolis, MN (US); Xin Su, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 42 days.

(21) Appl. No.: 15/704,893

(22) Filed: Sep. 14, 2017

(65) Prior Publication Data
US 2018/0078769 A1 Mar. 22, 2018

Related U.S. Application Data

(60) Provisional application No. 62/395,727, filed on Sep. 16, 2016.

(51) Int. Cl.
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/36007* (2013.01); *A61N 1/36062* (2017.08); *A61N 1/36071* (2013.01)

(58) Field of Classification Search
CPC .............. A61N 1/0551; A61N 1/36007; A61N 1/36062; A61N 1/36071; A61N 1/36139
See application file for complete search history.

(56) References Cited

U.S. PATENT DOCUMENTS

| 5,603,726 A | 2/1997 | Schulman et al. |
| 5,800,465 A | 9/1998 | Thompson et al. |
| 6,289,247 B1 | 9/2001 | Faltys et al. |

(Continued)

FOREIGN PATENT DOCUMENTS

| EP | 2396072 B1 | 3/2013 |
| WO | 2002009808 A1 | 2/2002 |

(Continued)

OTHER PUBLICATIONS

"St. Jude's Prodigy Neurostimulator with Burst Technology," Medgadget, Mar. 20, 2014, 4 pp.

(Continued)

*Primary Examiner* — Amanda K Hulbert
(74) *Attorney, Agent, or Firm* — Shumaker & Sieffert, P.A.

(57) ABSTRACT

This disclosure relates to methods, devices, and systems for delivering and adjusting stimulation therapy. In one example, a method comprising delivering, by a stimulation electrode, electrical stimulation as a candidate therapy to a patient according to a set of candidate therapy parameters, the stimulation electrode located in proximity to the dorsal column of a patient; sensing, by a sensing electrode, an electrically evoked compound action potential (eECAP) signal in response to the delivery of the electrical stimulation; and classifying, by a processor, the sensed eECAP signal generated in response to the application of the candidate therapy relative to an eECAP baseline is disclosed.

24 Claims, 12 Drawing Sheets

(56) References Cited

U.S. PATENT DOCUMENTS

| | | | |
|---|---|---|---|
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,333,858 | B2 | 2/2008 | Killian et al. |
| 7,577,480 | B2 | 8/2009 | Zeijlemaker |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 * | 9/2010 | Miesel ............... A61B 5/103 607/19 |
| 8,504,150 | B2 | 8/2013 | Skelton |
| 8,620,441 | B2 | 12/2013 | Greenberg et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 9,002,460 | B2 | 4/2015 | Parker |
| 9,138,582 | B2 | 9/2015 | Doan et al. |
| 9,155,892 | B2 | 10/2015 | Parker et al. |
| 9,339,655 | B2 | 5/2016 | Carbunaru |
| 9,381,356 | B2 | 7/2016 | Parker et al. |
| 9,386,934 | B2 | 7/2016 | Parker et al. |
| 2004/0267333 | A1 | 12/2004 | Kronberg |
| 2008/0221640 | A1 | 9/2008 | Overstreet et al. |
| 2011/0054570 | A1 | 3/2011 | Lane |
| 2011/0071589 | A1 | 3/2011 | Starkebaum et al. |
| 2011/0125223 | A1 | 5/2011 | Carbunaru et al. |
| 2012/0155188 | A1 | 6/2012 | Buettner et al. |
| 2013/0208390 | A1 | 8/2013 | Singh et al. |
| 2013/0268021 | A1 | 10/2013 | Moffitt |
| 2013/0289664 | A1 | 10/2013 | Johanek |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0243924 | A1 | 8/2014 | Zhu et al. |
| 2014/0243926 | A1 | 8/2014 | Carcieri et al. |
| 2014/0296936 | A1 | 10/2014 | Alataris et al. |
| 2014/0371813 | A1 | 12/2014 | King et al. |
| 2014/0378941 | A1 | 12/2014 | Su et al. |
| 2014/0379043 | A1 | 12/2014 | Howard |
| 2015/0127062 | A1 | 5/2015 | Holley et al. |
| 2015/0179177 | A1 | 6/2015 | Nagao |
| 2015/0360031 | A1 * | 12/2015 | Bornzin ............ A61N 1/36139 607/62 |
| 2016/0121124 | A1 | 5/2016 | Johanek et al. |
| 2016/0136420 | A1 | 5/2016 | Brink et al. |
| 2016/0157769 | A1 | 6/2016 | Min et al. |
| 2016/0175594 | A1 | 6/2016 | Min et al. |
| 2017/0209695 | A1 | 7/2017 | Solomon |

FOREIGN PATENT DOCUMENTS

| | | | |
|---|---|---|---|
| WO | 2010058178 | A1 | 5/2010 |
| WO | 2015143509 | A1 | 10/2015 |
| WO | 2015179177 | A1 | 11/2015 |
| WO | 2015179281 | A1 | 11/2015 |
| WO | 2016090420 | A1 | 6/2016 |
| WO | 2017106503 | A1 | 6/2017 |

OTHER PUBLICATIONS

Abejon MD, "Back pain coverage with spinal cord stimulation: A different treatment for each patient," International Neuromodulation Society. Jun. 10, 2015; 567, Abstract Only, 1 pp.

Abeloos MD, "High density stimulation as an alternative to uncomfortable cervical tonic spinal cord stimulation: case report," International Neuromodulation Society 12th World Congress, Jun. 11-15, 2015, Abstract Only, 1 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD, PhD, et al., "Effect of high-frequency alternating current on spinal afferent nociceptive transmission," Neuromodulation: Technology at the Neural Interface; Jul.-Aug. 2013;16(4): pp. 318-327.

Cui, et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder, et al., "Burst spinal cord stimulation for limb and back pain," World neurosurgery, Nov. 2013; 80 (5):642-649, e641.

De Ridder MD, PhD, et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res.,1313: (2010) available online Dec. 3, 2009 pp. 53-61.

Glider DO/PhD, et al., "High Frequency (1000 Hz) Stimulation Using Commercially Available Implantable Pulse Generator," North American Neuromodulation Society. Dec. 2013, Abstract Only, 2 pp.

Guan MD PhD, et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Guan et al., "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Holsheimer, "Computer modelling of spinal cord stimulation and its contribution to therapeutic efficacy," Spinal Cord Aug. 1998, 36: pp. 531-540.

Hunt SP, Mantyh PW. The molecular dynamics of pain control. Nat Rev Neurosci. Feb. 2001;2(2):83-91.

Kemler MD, et al., "Spinal cord stimulation in patients with chronic reflex sympathetic dystrophy," N Engl J Med, Aug. 31, 2000; 343(9):pp. 618-624.

Kilgore, PhD, et al., "Reversible Nerve Conduction Block Using Kilohertz Frequency Alternating Current," Neuromodulation. Aug. 2013, pp. 242-255.

Kumar, et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Sweet MD, et al., "High Frequency vs. Burst Stimulation Patterns for Dorsal Column Stimulation: The Importance of Charge," American Association of Neurological Surgeons, Abstract, Apr. 4, 2014, 2 pp.

Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.

North MD, et al., "Spinal cord stimulation versus repeated lumbosacral spine surgery for chronic pain: a randomized, controlled trial," Neurosurgery, Jan. 2005; 56(1): 98-106; discussion 106-107.

(56) References Cited

OTHER PUBLICATIONS

North MD, et al., "Clinical outcomes of 1 kHz subperception spinal cord stimulation (SCS): Results of a prospective randomized controlled crossover trial," Abstracts, International Neuromodulation Society, Jun. 2015, 1 pp.
Ranck Jr., et al., "Which elements are excited in electrical stimulation of mammalian central nervous system: a review," Brain Research, Nov. 21, 1975; 98(3): pp. 417-440.
Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the affective U.S. filing date of the present application, and any foreign priority date that the particular month of publication is not in issue.
Sato, et al., "Spinal cord stimulation reduces hypersensitivity through activation of opioid receptors in a frequency-dependent manner," Eur J Pain. Apr. 2013 (4): pp. 551-561, first published Oct. 5, 2012.
Song MD Phd., et aL, "Efficacy of kilohertz-frequency and conventional spinal cord stimulation in rat models of different pain conditions," Neuromodulation Jan. 2014; 17(3): pp. 226-234.
Schu MD, PhD., et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter MD, et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Maeda, et al., "Increased c-fos immunoreactivity in the spinal cord and brain following spinal cord stimulation is frequency-dependent," Brain Res. Mar. 9, 2009;1259: pp. 40-50, available online Jan. 6, 2009.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith, et al., "Successful use of high-frequency spinal cord stimulation following traditional treatment failure," Stereotact Funct Neurosurg. Apr. 1, 2015; 93(3): pp. 190-193.
Wille, MD, et al., "Altering Conventional to High Density Spinal Cord Stimulation: An Energy Dose-Response Relationship in Neuropathic Pain Therapy," Neuromodulation 2016, Aug. 2016, 9 pp.
Maggi, et al., "Effect of urethane anesthesia on the micturition reflex in capsaicin-treated rats." Journal of the Autonomic Nervous System, Jan. 1990, 30(3): 247-251.
Walter, et al., "Inhibiting the hyperreflexic bladder with electrical stimulation in a spinal animal model." Neurourology and Urodynamics, 1993, 12:241-253. doi:10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.
Hubscher, et al., "Convergence and cross talk in urogenital neural circuitries," J. Neurophysiol 110: 1997-2005, first published Aug. 7, 2013, 9 pp.
Snellings, et al., "Effects of stimulation site and stimulation parameters on bladder inhibition by electrical nerve stimulation," BJU International, Jul. 2012, pp. 136-143, first published Jan. 19, 2012.
Woock, et al., "Activation and inhibition of the micturition reflex by penile afferents in the cat," Am J. Physiol Regul Intergre Comp Physiol, published Apr. 23, 2008, pp. R1880-R1889.
International Search Report and the Written Opinion from International Application No. PCT/US2017/051885, dated Dec. 6, 2017, 13 pp.
International Preliminary Report on Patentability from International Application No. PCT/US2017/051885, dated Mar. 28, 2019, 7 pp.

* cited by examiner

DORSAL SPINAL COLUMN CHARACTERIZATION WITH EVOKED POTENTIALS

RELATED APPLICATION

This application claims the benefit of priority of U.S. Provisional Application Ser. No. 62/395,727, filed Sep. 16, 2016, the contents of which is incorporated herein in its entirety.

TECHNICAL FIELD

The disclosure relates to medical therapy and, more particularly, electrical stimulation.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, the heart, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads with percutaneous lead extensions.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, pelvic nerves, gastrointestinal organs, sacral nerves, peripheral nerves, or within the brain of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, this disclosure relates to adjusting electrical stimulation parameters associated with electrical stimulation delivered to a patient based on sensing of electrically evoked compound action potential (eECAP) in a patient. Various examples as described herein comprise using electrically evoked compound action potential (eECAP) as a tool to characterize nerve propagation or excitability changes in response to a specific therapeutic or diagnostic interventions, e.g., stimulation therapy, for example in the form of applied electrical stimulation, and using this information to inform and configure, e.g., optimize, future therapeutic modalities. The applied stimulation therapy may be configured, e.g., optimized, in a manner to suppress or enhance signal propagation on certain nerve fiber types, or to choose between equivalent stimulation therapies where one is more advantageous for other reasons (e.g., less current draw from the battery of the implanted medical device providing the applied stimulation therapy).

In various examples, the eECAP may be evoked in response to the application of electrical stimulation therapy defined according to a set of stimulation parameters. The sensed eECAP signal may be sensed and analyzed in view of one or more eECAP parameters, either directly measured from the sensed eECAP signal, or derived from the sensed eECAP signal. The eECAP parameters may then be used to determine whether one or more adjustments to the electrical stimulation parameters of the previously applied stimulation therapy can be made to better optimize a characteristic of the stimulation, and/or to better optimize operating parameters of the system providing the stimulation therapy. The eECAP signal can be sensed by a sensor which is located relatively further from the targeted stimulation nerve site, or a sensor which is placed in, or in close proximity to, the targeted stimulation nerve site. In some examples, the sensor can be built-in with one or more stimulation electrodes. In other examples, the same electrode, or electrodes, may be configured to deliver stimulation signals and detect the eECAP signal. In other examples, one or more of the electrodes configured to sense the eECAP are different from the electrode or electrodes configured to deliver the stimulation therapy.

In some examples, a method consistent with the disclosure includes a method comprising: delivering, by a stimulation electrode, electrical stimulation as a candidate therapy to a patient according to a set of candidate therapy parameters, the stimulation electrode located in proximity to the dorsal column of a patient; sensing, by a sensing electrode, an electrically evoked compound action potential (eECAP) signal in response to the delivery of the electrical stimulation; classifying, by a processor, the sensed eECAP signal generated in response to the application of the candidate therapy relative to an eECAP baseline; and determining, by the processor, if the sensed eECAP signal is different over the eECAP baseline based on at least one parameter used in classifying the sensed eECAP signal.

In some examples, the disclosure describes a system comprising: one or more electrodes; a stimulation generator configured to apply stimulation therapy via the one or more electrodes based on a set of stimulation therapy parameters; and a processor configured to: generate the candidate therapy parameters, control the stimulation generator to provide the candidate stimulation therapy to the one or more electrodes based on the candidate therapy parameters, sense an electrically evoked compound action potential (eECAP) signal generated in response to the application of the candidate stimulation therapy, classify the sensed eECAP signal based on an eECAP baseline; and determine if the sensed eECAP signal is different over the eECAP baseline based on at least one parameter used in classifying the sensed eECAP signal.

In some examples, the disclosure describes a system comprising: one or more electrodes; a stimulation generator configured to apply stimulation therapy via the one or more electrodes based on a set of stimulation therapy parameters; and a processor configured to: receive a detected signal including an evoked compound action potential (eECAP) in response to the application of the stimulation therapy; analyze the detected signal; and adjust at least one of the stimulation parameters based on the analysis of the detected signal.

In some examples, the disclosure describes a system comprising: means for applying stimulation therapy to a patient according to a set of stimulation therapy parameters; means for sensing a signal including an electrically evoked compound action potential (eECAP) in response to the application of the stimulation therapy; and means for classifying the sensed eECAP signal at least in part based on a baseline eECAP.

In some examples, the disclosure describes a non-transitory computer readable medium comprising instructions for causing a programmable processor to perform any of the methods described herein.

In some examples, a method consistent with the disclosure includes a method comprising: delivering, by a stimulation electrode, electrical stimulation as a baseline therapy to a patient according to a set of baseline therapy parameters, the stimulation electrode located in proximity to the dorsal column of the patient; sensing, by a sensing electrode, an electrically evoked compound action potential (eECAP) signal in response to the delivery of the electrical stimulation as an eECAP baseline; determining, by a processor, a change to a therapy parameter to generate a candidate therapy having a set of candidate therapy parameters; delivering, by the stimulation electrode, electrical stimulation based on the candidate therapy to the patient according to the candidate therapy parameters; sensing, by the sensing electrode, an electrically evoked compound action potential (eECAP) signal in response to the delivery of the electrical stimulation based on the candidate therapy; classifying, by the processor, the sensed eECAP signal generated in response to the application of the candidate therapy relative to an eECAP baseline; determining, by the processor, if the sensed eECAP signal is different over the eECAP baseline based on at least one parameter used in classifying the sensed eECAP signal; and establishing, by the processor, a parameter boundary for the at least one parameter as equivalent to the baseline if the sensed eECAP signal is determined to be different over the eECAP baseline.

In some examples, a method consistent with the disclosure includes a method comprising: delivering, by a stimulation electrode, electrical stimulation as a baseline therapy to a patient according to a set of baseline therapy parameters, the stimulation electrode located in proximity to the dorsal column of the patient; sensing, by a sensing electrode, an electrically evoked compound action potential (eECAP) signal in response to the delivery of the electrical stimulation as an eECAP baseline; generating, by a processor, a candidate therapy having a set of candidate therapy parameters; delivering, by the stimulation electrode, electrical stimulation as a candidate therapy to the patient accord to the set of candidate therapy parameters; sensing, by the sensing electrode, an electrically evoked compound action potential (eECAP) signal in response to the delivery of the electrical stimulation based on the candidate therapy; classifying, by the processor, the sensed eECAP signal generated in response to the application of the candidate therapy relative to an eECAP baseline; and determining, by the processor, if the sensed eECAP signal is different over the eECAP baseline based on at least one parameter used in classifying the sensed eECAP signal, wherein determining if the sensed eECAP signal is different over the eECAP baseline comprises deterring that the candidate therapy is equivalent to the baseline therapy if the sensed eECAP signal is not different over the eECAP baseline, or that the candidate therapy is not equivalent to the baseline therapy if the sensed eECAP signal is different over the eECAP baseline.

In some examples, a method consistent with the disclosure includes a method comprising: defining, by a processor, one or more target parameters for an electrically evoked compound action potential (eECAP) signal as a target eECAP; defining, by the processor, one or more candidate therapy parameters; generating, by the processor, a candidate therapy based on as set of the defined candidate therapy parameters; delivering, by a stimulation electrode, electrical stimulation based on the generated candidate therapy to a patient according to the set of candidate therapy parameters, the stimulation electrode located in proximity to the dorsal column of the patient; sensing, by a sensing electrode, an electrically evoked compound action potential (eECAP) signal in response to the delivery of the candidate therapy; classifying, by the processor, the sensed eECAP signal generated in response to the application of the candidate therapy relative to the target eECAP; and determining, by the processor, if the sensed eECAP signal matches the target eECAP based on at least one parameter used in classifying the sensed eECAP signal, wherein determining if the sensed eECAP signal matches the target eECAP comprises deterring that the at least one parameter used in classifying the sensed eECAP signal matches the corresponding parameter or parameters of the target eECAP.

In some examples, a method consistent with the disclosure includes a method comprising: delivering, by a stimulation electrode, electrical stimulation as a baseline therapy to a patient according to a set of baseline therapy parameters, the stimulation electrode located in proximity to the dorsal column of the patient; ceasing delivery of the electrical stimulation by the stimulation electrode; sensing, by a sensing electrode, an electrically evoked compound action potential (eECAP) signal in response to the delivery of the electrical stimulation as an eECAP signal; classifying, by a processor, the sensed eECAP signal generated in response to the application of the baseline therapy relative to an eECAP baseline; and determining, by the processor, if the sensed eECAP is a particular eECAP, the determination of whether the sensed eECAP is a particular eECAP based on one or more parameters used to classify the sensed eECAP signal; and determining, by the processor, if more therapy is to be delivered to the patient based on the determination of whether the sensed eECAP was or was not the particular eECAP.

In some examples, a method consistent with the disclosure includes a method comprising: delivering, by a stimulation electrode, electrical stimulation as a baseline therapy to a patient according to a set of baseline therapy parameters, the stimulation electrode located in proximity to the dorsal column of the patient; ceasing delivery of the electrical stimulation by the stimulation electrode; sensing, by a sensing electrode, an electrically evoked compound action potential (eECAP) signal in response to the delivery of the electrical stimulation as an eECAP signal; classifying, by a processor, the sensed eECAP signal generated in response to the application of the baseline therapy; determining, by the processor, if the sensed eECAP is a particular eECAP, the determination of whether the sensed eECAP is a particular eECAP based on one or more parameters used to classify the sensed eECAP signal; determining, by the processor, if a time period has expired following ceasing delivery of the electrical stimulation; and determining, by the processor, if more therapy is to be delivered to the patient based on the determination of whether the sensed eECAP was or was not the particular eECAP and whether the time period has expired.

The details of one or more examples are set forth in the accompanying drawings and the description below. Other features, objects, and advantages will be apparent from the description and drawings, and from the claims.

DETAILED DESCRIPTION

Figure 1:
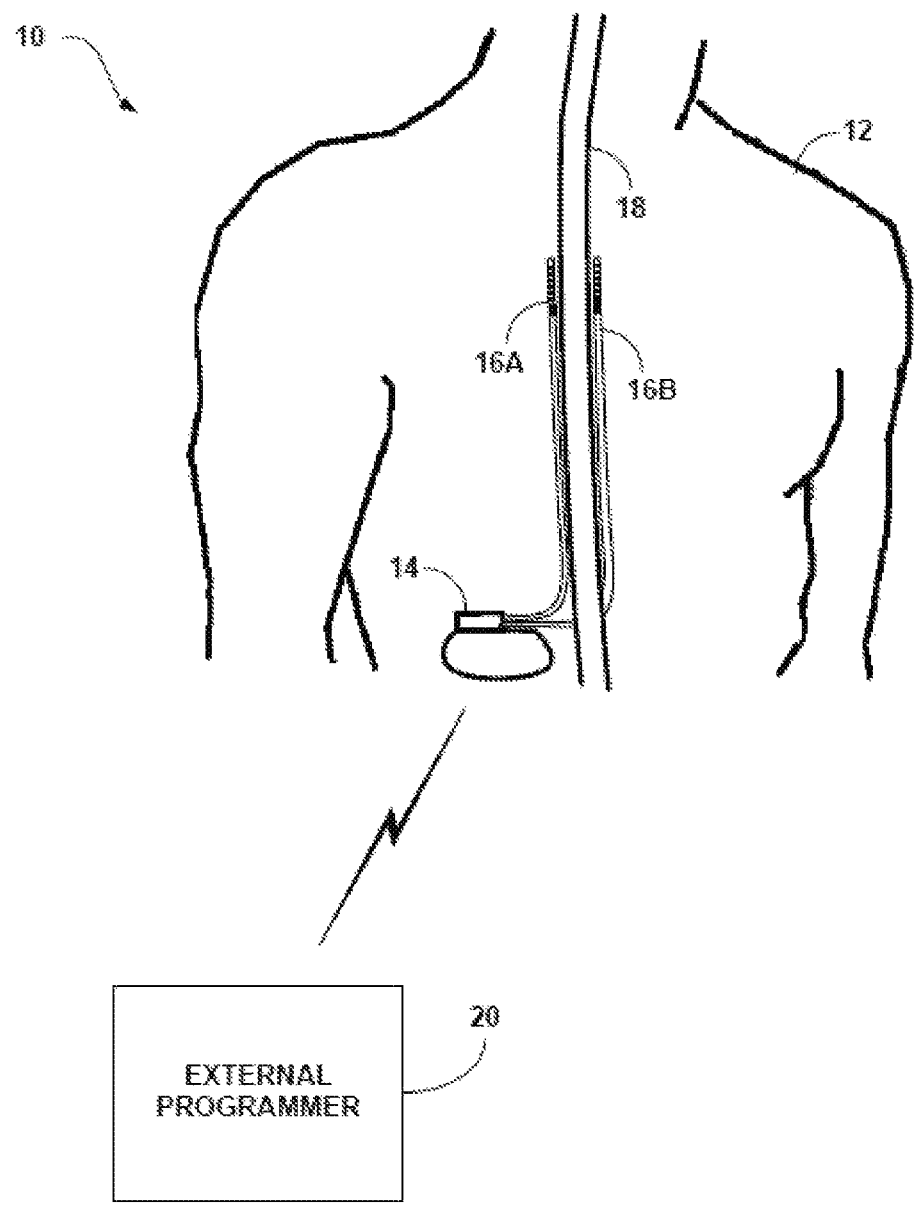
FIG. 1 is a schematic diagram illustrating an example implantable stimulation system including a pair of implantable stimulation electrode arrays carried by implantable leads.

This disclosure includes systems, devices, and methods relating to adjusting electrical stimulation parameters that define electrical stimulation delivered to a patient. A patient as used herein in general refers to a human patient, but is not limited to humans, and may include animals. Various references to a "test patient" as used herein may include animals used to receive test stimulation patterns and to collect data related to the stimulation tests according to the various techniques described herein. In therapeutic or intervention type applications, a patient may receive electrical stimulation therapy to relieve a variety of symptoms or conditions. In some cases, a physician or clinician may manually adjust electrical stimulation parameters according to patient feedback, such as the patient's perception on reduction in pain levels or any changes in symptoms. However, patient feedback can be inconsistent over time and it is also subjective. In this manner, it may be difficult to determine the most appropriate stimulation parameters to relive the patient's symptoms or conditions and provide improved system performance (e.g., efficient energy usage and targeted therapy delivery).

As discussed herein, systems, devices, and methods are described for adjusting electrical stimulation parameters based on a detected electrically evoked compound action potential (eECAP). The eECAP may be evoked in response to the application of electrical stimulation therapy that is defined according to a set of stimulation parameters. Adjustments to the electrical stimulation parameters based on the detected eECAP may provide more objective information than patient feedback. In addition, eECAP detection may allow a system to provide closed-loop stimulation control. Incorporation of eECAP into adjustment, and/or titration, of stimulation parameters may allow for stimulation systems to provide stimulation therapy that uses less energy, more targeted stimulation delivery to desired tissues, and/or improved therapeutic efficacy as compared to techniques that do not incorporate eECAP detection. In some examples, dorsal column stimulation therapy or other electrical stimulation therapy is provided according to a therapy program with stimulation parameters, such as current or voltage amplitude, frequency, and/or pulse width, that are selected to provide a level of therapy, such as a reduction in the level of or elimination of pain felt by the patient. Spinal cord stimulation may also include stimulation of dorsal nerve roots. Further, stimulation is not limited to stimulation of the spinal cord, and may be applied to peripheral nerves or their end organs. Further, peripheral stimulators do not have to be implanted devices, and they may also comprise non-electrical stimuli (e.g., mechanical, thermal).

Spinal cord stimulation (SCS) in patients has historically consisted of fixed lower frequency, (e.g., approximately 50 Hz), periodic delivery of electrical impulses to the dorsal column of the patient for the purpose of inducing paresthesia. The paresthesia serves to mask pain felt in specific regions of the body, such as the lower back or legs. Sensory signals, in this case, the periodic electrical impulses from the spinal cord stimulator or the pain signal itself, are relayed to the brain via the dorsal columns of the spinal cord. The dorsal column consists of multiple sensory nerve fiber types, categorized generally by the fiber thickness and their associated signal propagation velocities. Very thick (13-20 μm) Aα fibers have action potential propagation velocities around 100 m/s and are associated with proprioception. Thick diameter (6-12 μm) Aβ fibers are heavily myelinated with action potential propagation velocities approaching 60 m/s. Paresthesia with SCS is thought to result from modulation of Aβ fibers. Thinner diameter (2-5 μm), myelinated Aδ fibers have action potential propagation velocities on the order of 10 m/s. Unmyelinated C fibers (0.2 μm-1.5 μm) transmit signals at 2 m/s. Both Aδ and C fibers are responsible for transmitting pain signals to the brain, with Aδ and C fibers contributing acute and burning pain characteristics, respectively. The dorsal column is part of an ascending pathway, comprising nerve such as Aα Type I or Aα Type II nerve fibers, that is important for fine touch and conscious proprioception.

There are a number of factors which may affect the propagation of signals along the spinal cord. Examples include the presence or absence of certain chemical factors, disease state, or electrical stimulation. In some instances, it is desirable to adapt a therapeutic intervention with a patient based on the measured signal propagation characteristics of the spinal cord. One method for quantifying these characteristics is with the electrically evoked compound action potential (eECAP). In various examples, an electrical stimulus is applied to the spinal cord of a patient at a particular location, and the resultant eECAP is recorded. The sensing and measurement of these eECAP signals are not limited to the spinal cord, and may also be recorded in other locations besides the spinal cord, such as peripheral nerves, or for example from within the brain.

In view of these factors, other parameters for delivery of SCS therapies that are different from the historically applied SCS therapies may provide efficacy in treatment for a particular patient. For example, SCS systems which deliver stimulation at a higher frequency, for example at a 10 kHz frequency are known, which utilize a much faster frequency than traditional SCS therapies provided at the 50 Hz frequency. The asserted advantage of the application of the higher frequency therapy is that patients have reported masking of the pain sensation(s) without the associated paresthesia sensation sometimes experienced when using the lower frequency SCS therapies. However, at least one drawback to these higher frequency systems is the need for extremely frequent battery recharge owing to the two-hundred times faster stimulation frequency. Further, these higher frequency systems can lose efficacy and require more frequent in-clinic therapy updates over traditional systems that deliver the lower frequency SCS therapies. For patients where 10 kHz neurostimulation results in adequate short term therapy but is unacceptable from a battery draw-down and durability perspective, characteristics of the eECAP, as described herein, may be used to select an alternative stimulation paradigm which results in significantly less battery-referred current consumption and is more robust against anticipated efficacy loss, while maintaining a same or at least an adequate level of efficacy for the patient's symptoms.

As noted above, the systems, devices, and methods described herein relate to using the eECAP as a tool to characterize nerve propagation changes in response to specific therapeutic or diagnostic interventions (stimulation therapy), and using this information to inform and optimize future therapeutic modalities. The therapy provided may be optimized in a manner to suppress or enhance signal propagation on certain fiber types in a patient, or to choose between equivalent therapies where one is more advantageous for other reasons (e.g., less current draw from the battery of the implanted medical device delivering the therapy). The eECAP may be evoked in response to the application of electrical stimulation therapy that is defined according to a set of stimulation parameters. Adjustments to the electrical stimulation parameters based on the detected eECAP may provide more objective information than patient feedback. In addition, eECAP detection may allow a system to provide closed-loop stimulation control. Incorporation of eECAP into adjustment, and/or titration, of stimulation parameters may allow for stimulation systems to provide stimulation therapy that uses less energy, more targeted stimulation delivery to desired tissues, and/or improved therapeutic efficacy as compared to techniques that do not incorporate eECAP detection. The eECAP may be detected by an electrical sensing system such as one within an implantable medical device, or in electrical communication with said device. The sensing system may include one or more electrodes positioned at some distance away from the site of the application of the electrical stimulation.

In some examples, detection, or the lack thereof, of the presence of the eECAP in response to stimulation provided at a particular set of therapy parameters is used to program initial stimulation therapy parameters provided to a patient via an implantable medical device. In other examples, the detection of eECAP in response to stimulation provided at a particular set of therapy parameters may be used to adjust existing stimulation therapy parameters. The programming or adjustment of stimulation therapy parameters may be manual or automatic. The presence or absence of an eECAP in response to a set of stimulation therapy program may be used as a biomarker in programing and adjustment to patient stimulation.

For example, during initial programming, an IMD may start providing stimulation according to an initial therapy parameter set, e.g., including a relatively higher frequency, such as 15 kHz. An eECAP signal that is generated by one or more nerve fibers as a result of the applied stimulation is sensed, and may then be stored as a baseline signal. Following establishment of the baseline, one or more parameters of the stimulation therapy may be adjusted. For example, the frequency of the applied stimulation is lowered in order to generate a new set of therapy parameters for a candidate therapy. The candidate therapy is then applied to the patient, and the resulting eECAP generated as a result of the application of the candidate therapy is sensed and categorized with respect to the stored baseline signal.

Categorization of the baseline eECAP signal and the eECAP signal generated in response to the applied candidate therapy or candidate therapies is not limited to any particular type of categorization, and refers to any type of analysis of the eECAP signals. Categorization may include quantification of any type of parameter the can be either directly measured from an eECAP signal, or derived from a measurable parameter of an eECAP signal. An example of a parameter associated with an eECAP signal would include determination of an amplitude of the eECAP signal at some predetermine time following cessation of the application of the electrical stimulation therapy. Examples of parameters associated with an eECAP signal are not limited to any particular parameter or type of parameter. Further non-limiting examples of parameters associated with eECAP signals are provided throughout this disclosure.

In various examples, one or more of the parameters of the eECAP signal are determined, the eECAP parameters derived from an initial stimulation therapy having known therapy parameters as provided to a patient, wherein the eECAP parameters and eECAP are stored as part of a baseline. A candidate therapy having one or more therapy parameters that are different from the therapy parameters of the initial stimulation therapy are generated, and applied to the patient. The eECAP signal generated in response to each of the applied candidate therapies is sensed, and one or more parameters related to the sensed eECAP generated in response to the applied candidate therapy are determined, and compared to the parameters stored with respect to the baseline. By comparing the parameters of the eECAP generated in response to the applied candidate therapy to the baseline parameters, a determination may be made as to whether the eECAP generated in response to the applied candidate therapy is different from the eECAP generated by the initial stimulation therapy.

The determination of "different from" is not limited to any particular criteria, and for example may be based on whether a particular parameter determined for the eECAP generated in response to the applied candidate therapy falls within a predefined range of values with respect to the value for that same parameter determined for the eECAP signal generated in response to the application of the initial stimulation therapy, e.g., the baseline value for that parameter. The criteria used for making the determination as to whether the eECAP signal generated in response to the application of the candidate therapy is different from the eECAP signal generated in response to the application of the initial stimulation therapy are not limited to any particular criterial, as many parameters associated with eECAP signals are possible, and are contemplated by at least the examples, and the equivalents thereof, as further provided in this disclosure. Using these techniques, a candidate therapy that provides the same (i.e., not different from) eECAP response as the initial therapy, based on one or more compared parameters, but using a different set of therapy parameters may be determined using the measured eECAP as the basis for performing the comparisons. By using a different set of therapy parameters, the candidate therapy may therefore provide an equal or a substantially equal level of treatment efficacy to the patient while providing other performance advantages, such as longer battery life between recharges or battery replacements, compared to the initial stimulation therapy.

In other examples, the baseline parameters are associated with a target eECAP response that is not necessarily a result of a sensed eECAP resulting from applied stimulation therapy, but instead a proposed response. In various examples, one or more candidate therapies having a set of therapy parameters are proposed, and the candidate therapies are generated and applied to the patient. The sensed eECAP signal generated in response to each of the applied candidate therapies can then be sensed and analyzed to determine if the candidate therapy resulted in an eECAP signal the meets one or more criteria established for the target eECAP. The criteria for determining if the candidate therapy resulted in generation of the target eECAP is not limited to any particular criteria, and in some examples may be based on a determination that one or more of the parameters associated with the eECAP generated by application of the candidate therapy falls within a predetermined range of the value of the corresponding parameter of the target eECAP response, or exceeds a threshold value set by the corresponding parameter of the target eECAP response.

In various examples, the adjustment to the therapy parameters used to generate the candidate therapies may include an increase or may include a decrease in any of the therapy parameters of the applied stimulation, for example, by adjustment to the amplitude, frequency and/or pulse width of stimulation pulses. In some examples, the stimulation intensity may be increased or decreased at predetermined increments, and each incremental adjustment of the parameters may be used to generate a new candidate therapy that can then be applied, at separate times to the patient in order to generate an eECAP that may be sensed and analyzed with respect to the efficacy and other properties of the associated candidate therapy.

In some examples, a given stimulation therapy may be applied to a patient, and the resulting eECAP signal sensed and analyzed to determine whether the patient's response to that same particular set of stimulation parameters has changed. In some examples, detection of the eECAP signal in response to a current stimulation therapy program is performed on an ongoing basis. For example, eECAP signal may be detected every few seconds, once a minute, once every few minutes, hourly, daily or weekly. In some examples, an eECAP signal may be detected in response to a change in another sensed physiological parameter. For example, the eECAP may detected when there has been a change in activity level or posture of the patient. These changes in activity level and/or posture of a patient may be sensed and/or determined by a same device providing the stimulation therapy to the patient, or by devices that are not the same devices providing the stimulation therapy to the patient.

FIG. 1 is a schematic diagram illustrating an example implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1, system 10 includes an IMD 14 and external programmer 20 shown in conjunction with a patient 12. In the example of FIG. 1, IMD 14 is an implantable electrical stimulator configured for spinal cord stimulation (SCS), e.g., for relief of chronic pain or other symptoms. Again, although FIG. 1 shows an implantable medical device, other embodiments may include an external stimulator, e.g., with percutaneously implanted leads, or implanted leads with percutaneous lead extensions. Stimulation energy is delivered from IMD 14 to spinal cord 18 of patient 12 via one or more electrodes disposed on implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16, e.g., in bipolar, unipolar, or multipolar combinations. The target tissue may be any tissue affected by electrical stimulation energy, such as electrical stimulation pulses or waveforms. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead. Other electrode and lead configurations may be adapted for use with the present disclosure so long as they enable IMD 14 to electrically stimulate and sense from a target tissue.

In the example of FIG. 1, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), sacral neuromodulation (SNM), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, and a pulse rate, for stimulation pulses delivered by IMD 14 according to that program. The program may also define an electrode combination for delivery of the stimulation pulse, including electrode polarities. Moreover, therapy may be delivered according to multiple programs, wherein multiple programs are contained within each of a multiple of groups.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may be decreased to avoid causing patient 12 additional pain or unusual sensations, which may be considered undesirable side effects that undermine overall efficacy.

Also, posture state changes may present changes in symptoms or symptom levels, e.g., pain level. Reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically detect an eECAP response to stimulation in response to a change in posture state. Based on the detected eECAP, IMD 14 determines whether an adjustment to the stimulation parameters is recommended or otherwise appropriate. For example, a posture state module may include a posture state sensor, such as an accelerometer, that detects when patient 12 lies down, stands up, or otherwise changes posture.

A posture state module may include, for example, one or more accelerometers that detect when patient 12 occupies a posture state in which it may be appropriate to decrease the stimulation amplitude, e.g., when patient 12 lies down. In some examples, the IMD may automatically reduce stimulation amplitude so that patient 12 does not manually have to do so. The IMD may then detect an eECAP biomarker in response to the adjusted stimulation parameters to determine if the adjustment was effective. In other examples, the IMD may detect an eECAP biomarker in response to stimulation when a change in posture is detected prior to making an adjustment to the stimulation parameters. IMD 14 may analyze the detected eECAP biomarker to determine the appropriate adjustment to the stimulation parameters. Example posture states may include "Upright," "Upright and Active," "Lying Down," and so forth.

As will be described in greater detail below, in some examples, IMD 14 may be configured to automatically adjust stimulation amplitude when it detects that patient 12 has changed position. In some examples, in response to detection of a change in position, IMD 14 determines an appropriate adjustment to the stimulation parameters. In some examples, the determination may include detecting eECAP based on the current stimulation parameters, and making adjustments to one or more stimulation parameters based on the eECAP biomarker detected. In other examples, IMD 14 may select a new set of stimulation parameters stored in a memory based on previously detected eECAP for the same position.

In some examples, stimulation parameter may be configured to be changed at a rate suitable to prevent undesirable effects, e.g., such as the effects due to the compression of leads 16 towards spinal cord 18 when patient 12 lies down. In some examples, IMD 14 may be configured to decrease the stimulation amplitude to a first predetermined lower amplitude value substantially immediately upon detection by IMD 14 that patient 12 is lying down. IMD 14 may then evaluate the appropriateness of the new stimulation amplitude based on eECAP, and make further adjustments as necessary. In other examples, IMD 14 may be configured to detect an eECAP biomarker to stimulation upon detection of patient 12 lying down. Based on the detected eECAP biomarker, IMD 14 may adjust one or more stimulation parameters until a desired eECAP biomarker is achieved.

In response to a posture state indication by the posture state module, IMD 14 may change a program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. The amount of automatic reduction may be determined, at least in part, based on a detected eECAP biomarker in the new posture state. In some cases, IMD 14 may communicate with external programmer 20 to present a proposed change in stimulation in response to a posture state change, for example for a first posture state to a second posture state, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

In some examples, IMD 14 may periodically detect eECAP generated in response to current stimulation parameters and adjust the current stimulation parameters if there has been a significant change, i.e., greater than a predetermined threshold change, to the detected eECAP biomarker relative to a desired or reference eECAP biomarker. IMD 14 may detect and analyze eECAP on an hourly, daily, weekly, or monthly basis for example. In some examples, IMD 14 may initiate an eECAP biomarker detection and analysis cycle if a predetermined amount of time has passed since the last eECAP biomarker detection. The time may reset any time an eECAP biomarker is detected.

Referring still to FIG. 1, a user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A program group may be characterized by multiple programs that are delivered simultaneously or on an interleaved or rotating basis.

During the delivery of stimulation therapy, patient 12 may make patient therapy adjustments, i.e., patient adjustments to one or more parameters of a therapy via an input device of a user interface of a programmer, to customize the therapy either after patient 12 moves to a different posture state or in anticipation of the next posture state. In some examples, IMD 14 may detect an eECAP in response to the therapy adjustment. In some examples, the detected eECAP in response to the adjusted therapy may be stored as indicating effective therapy for a particular patient state. If the same patient state is detected again, IMD 14 may automatically adjust one or more stimulation parameters in order to achieve an eECAP biomarker which corresponds to the stored eECAP biomarker. In examples where IMD 14 is in a record mode to store all patient therapy adjustments associated with a specific patient state, IMD 14 may implement a method to ensure that patient therapy adjustments are associated with the correct patient state intended by patient 12 when the therapy adjustment was made. The patient 12 may occupy the patient state multiple times such that there are multiple instances of the sensed patient state. A patient state may be a posture or activity level, for example. In some examples, each time the patient 12 occupies a posture state, the patient may enter one or more therapy adjustments.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use, either manually or via other user input media.

External programmer 20 may present eECAP biomarker data stored in IMD 14 from the detected eECAP biomarkers to various patient states of patient 12. The eECAP data may be acquired by external programmer 20 from IMD 14 to generate patient state information, e.g., changes in eECAP biomarker and associated therapy adjustment. IMD 14 may also store any associations between changes in eECAP response, therapy adjustments, and the patient states for which the therapy adjustments were intended during a record mode, i.e., therapy adjustment information. By recording all therapy adjustments made for a program in each of the patient states, including each of the multiple instances of the sensed patient states, external programmer 20 may be able to present therapy adjustment information to the user that indicates a desired eECAP biomarker and corresponding stimulation parameters based upon parameter use. For example, the user may be able to identify the most recent stimulation parameters desired by patient 12, the minimum and maximum allowable amplitudes, or even the quantified number of therapy adjustments to indicate that patient 12 is either satisfied with a program or cannot readily find suitable parameters for a program with many therapy adjustments.

The therapy adjustment information stored during the record mode may be presented in any number of different manners. For example, an output device of the user interface may present each program of a group and the respective number of therapy adjustments and the range of such amplitudes defined by the therapy adjustments. Alternatively, an output device of the user interface may also, or instead, present the last (i.e., most recent) amplitude used by patient 12 to deliver therapy with each program. In any manner, the therapy adjustment information may be presented in a graphical, numerical, or textual mode on external programmer 20. The user may be able to customize the presentation of the therapy adjustment information in other examples.

In some examples, external programmer 20 may utilize the associations of the eECAP signal and the therapy adjustments, to posture states in order to further minimize time needed to program all therapy programs. When presenting the amplitude ranges of the therapy adjustments for each therapy program, the user may be able to provide a single confirmation input that sets the amplitude for all programs to some nominal therapy parameter, for example. The nominal therapy parameter may be a minimum amplitude associated with the program and posture state, the last amplitude associated with the program and posture state, or some other therapy parameter already stored by IMD 14 in association with each therapy program and posture state. The therapy parameter may be referred to as nominal in the sense that it refers to a parameter value by a name that is descriptive of the value, rather than to a specific, absolute parameter value. In cases where a program has not been associated with any therapy adjustment, no new stimulation parameter may be programmed to the program.

In other examples, external programmer 20 may, using a guided algorithm, generate a suggested therapy parameter based upon an eECAP biomarker resulting from delivery of the therapy according to current stimulation therapy parameters. In some examples, the current stimulation therapy parameters may be a base stimulation therapy program. The suggested therapy parameter may be a specific therapy parameter value that is visible to the user, but is signified as being suggested by the guided algorithm. The guided algorithm may be an equation, set of equations, look-up table, or other technique for generating a suggested therapy parameter that may define stimulation therapy that may be effective when delivered to patient 12. In this manner, external programmer 20 analyzes the eECAP biomarker resulting from previous therapy adjustments for the most appropriate stimulation parameters that fit the desires of the user. The guided algorithm may generate a low or high weighted average, a safe average that minimizes the chances of overstimulation, a trend target that weights more recent patient adjustments to therapy greater than older therapy adjustments, or even an intergroup average that looks to therapy adjustments to programs in different groups that provide stimulation therapy. In any case, the user may be able to program the plurality of programs with each suggested therapy parameter with the selection of a single confirmation input.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. The electrodes may pierce or affix directly to the tissue itself. In general, ring electrodes arranged at different axial positions at the distal ends of leads 16 will be described for purposes of illustration.

Figure 2:
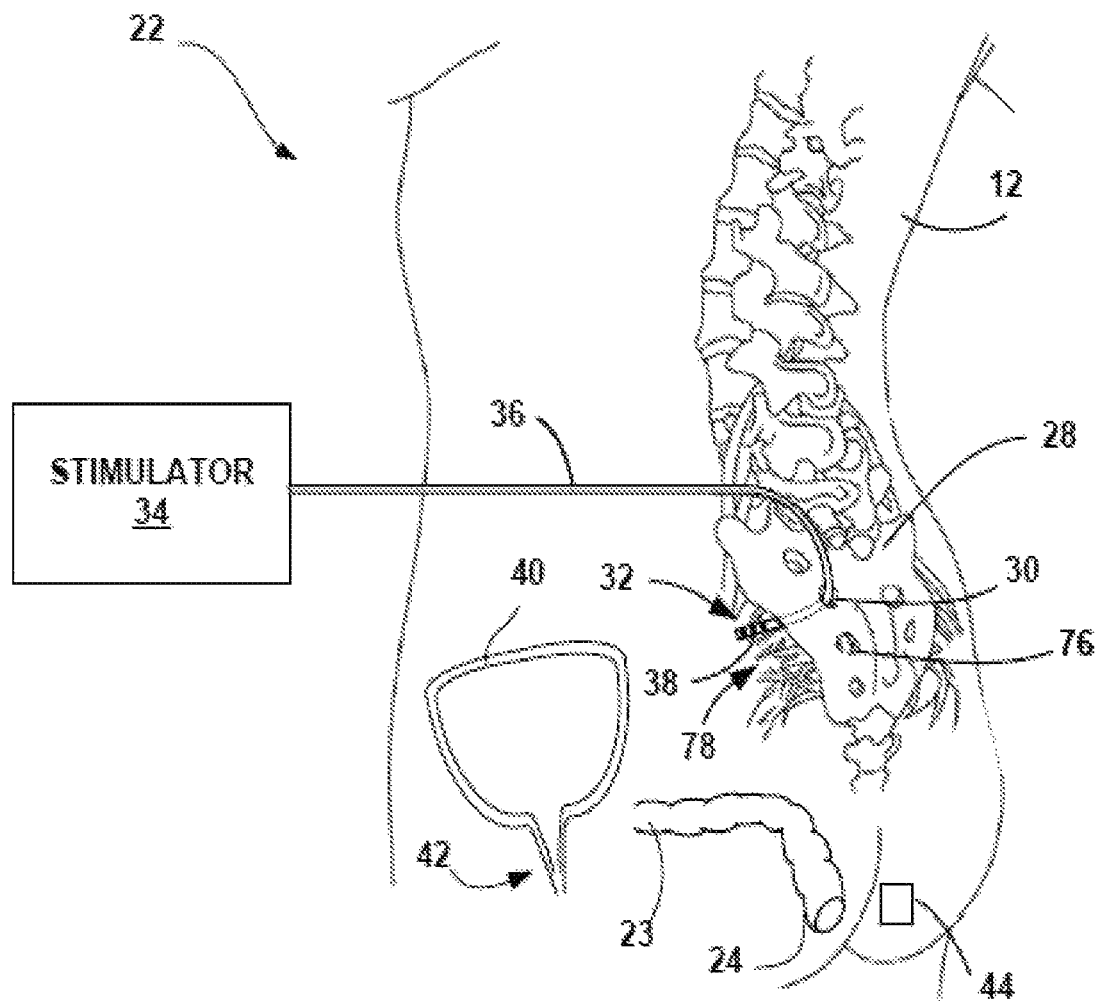
FIG. 2 is a conceptual diagram illustrating an example system that is configured to deliver sacral neuromodulation to a patient.

FIG. 2 is a conceptual diagram illustrating an example system 22 that is configured to deliver sacral neuromodulation to patient 12. As shown in in FIG. 2, system 22 includes stimulator 34 (e.g., and electrical stimulator or IMD) coupled to a medical lead 36 carrying electrodes 38 near a distal end of lead 36. System 22 may also include an optional electrode patch 44. In examples where stimulator 34 is external, lead 36 may be connected to a lead extension (not shown) passing through the skin and coupled to stimulator 34. Stimulator 34 may deliver electrical stimulation at least partially defined by a set of therapy parameter values (e.g., current amplitude, voltage amplitude, pulse width, pulse frequency, and electrode combination). In some examples, system 22 may be configured to provide peripheral nerve stimulation, e.g. sciatic nerve stimulation, tibibial nerve stimulation, or stimulation at a surface of a painful dermatome (e.g., low back or leg), for example applied to a patient having lower back pain who have SCS therapy. The configuration of system 22 for such stimulation may include location of the electrodes of the lead proximate to such nerves. An evoked potential from the SCS lead can be captured by stimulating nerves innervating in the low back. Therefore, this potential will be an objective readout of pain symptom and efficacy marker. In various examples, peripheral stimulation could include other stimulation modalities in addition to electrical stimulation, e.g., mechanical, cold, and heat stimulation.

Although a single lead 36 is shown, two or more leads may be used in other examples. For example, system 22 may include a second lead in order to provide bilateral neuromodulation. Bilateral neuromodulation may be provided alternatively or simultaneously depending upon the symptoms or disease being treated. For example, a stimulation pulse may be applied on both sides of the midline at the same time. In other examples, stimulation may be provided by first one lead to one side, and then by the other lead, to the other side. In some examples, the intensities of stimulation applied by each lead or for each nerve may be adjusted individually based on an eECAP response to stimulation from each lead, or to each nerve.

Stimulator 34 may include a therapy delivery module and/or other components configured to deliver, via lead 36 and one or more electrodes 38, electrical stimulation to a sacral nerve 32 that may potentially provide therapy to control fecal or urinary incontinence, for example. Fecal incontinence may refer to a condition of involuntary loss of fecal matter, and may include urge incontinence, stress incontinence, or both stress and urge incontinence, which may be referred to as mixed incontinence. As used in this disclosure, the term "fecal incontinence" includes disorders in which fecal matter is voided (i.e., defecation) when not desired, such as stress or urge incontinence, and disorders in which fecal voiding does not occur as desired, such as irritable bowel syndrome. Urinary incontinency may refer to a condition of loss of bladder control, and may include urge incontinence, stress incontinence, or both stress and urge incontinence, which may be referred to as mixed incontinence. As used in this disclosure, the term "urinary incontinence" includes disorders in which urine is voided when not desired, such as stress or urge incontinence, and disorders in which urinary voiding does not occur as desired, such as diabetes. Similar to fecal incontinence, urinary incontinence or other pelvic floor disorders (e.g., sexual dysfunction) may also result from a lack of voluntary control and may be treated with electrical stimulation, pharmaceuticals, or other therapies. In some examples where stimulator 34 is used to treat fecal incontinence, stimulation may be applied to the second sacral nerve. In some examples where stimulator 34 is used to treat urinary incontinence, stimulation may be delivered to the third sacral nerve. Although discussed with respect to therapy for bladder and bowel dysfunctions, system 22 may be used to treat other pelvic floor conditions, to provide peripheral nerve simulation for chronic pain or sexual dysfunction, or other treatments based on stimulation applied to one or more sacral nerves.

Although only two electrodes 38 are shown on lead 36, system 22 may include three or more electrodes in other examples. In addition, electrodes 38 may be implantable or at least partially implantable in other examples. For example, lead 36 may be transcutaneous or electrodes 38 may be part of a fully implantable device for sensing and monitoring eECAP signals. In examples, including two leads, each lead may include two or more electrodes. In some examples, one electrode may be used for sensing, while another is used for providing simulation. The electrodes may be on the same lead or on different leads. Stimulation may be provided ipsilaterally or contralaterally.

Patient 12 includes intestines 23 that may be subject to a condition such as fecal incontinence. Intestines 23 may include a descending colon, a sigmoid colon, rectum 24 and an anus. During normal, or healthy function of intestines 23, the sigmoid colon and rectum 24 are depicted such that their position relative to one another form a "valve" or "fold" that prevents fecal matter from entering rectum 24. During a fecal voiding event, however the sigmoid colon and rectum 24 may shift to positions that open the value or fold thereby allowing fecal matter in the sigmoid colon to pass to rectum 24 and exit the anus. When fecal matter is present in the sigmoid colon or rectum 24, patient 12 may typically recognize the sensation and take action (e.g., prevent fecal voiding or voluntarily void the fecal matter). However, for a patient with fecal incontinence, patient 12 may not recognize the sensation of fecal matter or be able to voluntarily control the need to void.

Although fecal incontinence may be caused by muscular or neurological dysfunction, sensations and stimulation of pelvic floor nerves and/or sensed eECAP signals may still be useful for identifying therapies that may be effective in treating the condition of patient 12. For example, eECAP signals may be detected by electrodes 38 indicating that nerves in the area near rectum 24 are being activated by applied stimulation. In some examples, eECAP signals may be detected during initial programming of SNM device such as the one in system 22. For example, stimulation intensity may be slowly raised, e.g., by adjusting one or more of voltage or current amplitude, pulse width or pulse rate, until an eECAP biomarker is first detected. Ongoing stimulation therapy is then provided by stimulator 34 at an intensity level below the level which resulted in an eECAP biomarker.

In some examples, the stimulation intensity may be set to 50%, 80%, or 90% of the stimulation intensity resulting in the eECAP biomarker, for example. If voltage or current pulse amplitude is adjusted, for example, the amplitude may be set to 50%, 80%, or 90% of the amplitude that resulted in the eECAP biomarker.

In some examples, the set of therapy parameter values selected for electrical stimulation to treat fecal incontinence may include pulses delivered at a certain frequency. For example, if stimulation comprises delivery of pulses, the pulse frequency may be selected from a range between 0.05 Hz and 50 Hz. In another example, the pulse frequency may be selected from a range between 0.1 Hz and 25 Hz. In still another example, the pulse frequency may be selected from a range between 0.5 Hz and 15 Hz. In one example, the pulse frequency may be selected from between approximately 1.0 and 3.0 Hz. These frequencies may elicit cortical evoked potentials and therapy related to fecal incontinence. However, these frequencies may also be effective in treating other disorders such as urinary incontinence or sexual dysfunction.

Stimulator 34 may also include a therapy delivery module and/or other components configured to deliver, via lead 36 and one or more electrodes 38, electrical stimulation to second sacral nerve 32 (i.e., S2) or other nerve that may potentially provide therapy to control the fecal incontinence of patient 12. In the example shown in FIG. 2, the distal end of lead 36 is inserted into sacral foramen 30 of sacrum 28. Since second sacral nerve 32 may be known to innervate portions of intestines 23 such as rectum 24, electrodes 38 may be implanted adjacent to second sacral nerve 32 to evaluate the efficacy of therapy delivered to this site. In this manner, the second sacral nerve 32 may be associated with the anatomical regions of intestines 23 and rectum 24. A nerve or nerves which innervate or otherwise carry impulses to or away from an anatomical region may be referred to as a nerve associated with the anatomical region. In other examples, stimulation of second sacral nerve 32 may be performed using electrodes external of the pelvic floor either subcutaneously implanted or placed on the external surface of the skin. However, these other locations may not be sufficiently precise to evaluate stimulation therapy. In some examples, stimulation may be delivered to second sacral nerve 32 and additional nerves adjacent to the sacral nerve. For example, stimulation may be delivered to both S2 and S3 nerves.

In examples directed to treating fecal incontinence, stimulator 34 may be configured to deliver electrical stimulation to second sacral nerve 32 according to a selected set of stimulation therapy parameter values. This set of therapy parameter values may at least partially define the electrical stimulation and include parameter values for one or more therapy parameters such as current amplitude, voltage amplitude, pulse width, pulse frequency, waveform shape (in examples that include continuous waveform delivery) and electrode combinations. The set of therapy parameter values may be selected according to clinician experience, patient condition, or any other circumstances. Fecal incontinence may also be treated by stimulating one or more other nerves in addition or alternative to second sacral nerve 32. For example, stimulation may be directed to one or more of a pelvic floor nerve, a pelvic floor muscle, the anal sphincter, or other pelvic floor targets. Pelvic floor nerves include peripheral nerves such as sacral nerves, pudendal nerves and associated branches, and dorsal genital nerves.

In the example shown in FIG. 2, lead 36 is cylindrical. Electrodes 38 leads 36 may be ring electrodes, segmented electrodes, or partial ring electrodes. Segmented and partial ring electrodes each extend along an arc less than 360 degrees (e.g., 90-120 degrees) around the outer perimeter of lead 36. In some examples, lead 36 may have a complex electrode geometry. An example of a complex electrode array geometry may include an array of electrodes located at different axial positions along the length of a lead in addition to electrodes located at different angular positions about the periphery, e.g., circumference, of the lead 36. In examples, lead 36 may be, at least in part, paddle-shaped (i.e., a "paddle" lead), e.g., where an array of electrode pads is provided in a two-dimensional array on a surface of the paddle lead. In some examples, one or more of electrodes 38 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12. An electrical field represents the areas of a patient anatomical region that will be covered by an electrical field during delivery of stimulation therapy to tissue within patient 12. The electrical field may define the volume of tissue that is affected when the electrodes 38 are activated. An activation field represents the neurons that will be activated by the electrical field in the neural tissue proximate to the activated electrodes.

Additionally, or alternatively, system 22 may be configured to control delivery of electrical stimulation and sense eECAP biomarkers to screen for effective therapy to treat a bladder related condition of patient 12. In some examples directed to treatment of bladder related conditions, lead 36 may directed through sacral foramen 76 in order for stimulator 34 to deliver electrical stimulation to third sacral nerve 78 via one or more electrodes 38 of lead 36. Third sacral nerve 78 may innervate anatomical regions associated with urinary incontinence such as the muscular wall of bladder 40 and urinary sphincter 42. Additional or alternative nerves may also be targeted by one or more of electrodes 38.

As discussed above with respect to fecal incontinence, stimulation may be applied to third sacral nerve 78 while a signal is monitored for an eECAP biomarker via electrodes 38. During programming, stimulation intensity may be incrementally raised until an eECAP biomarker appears in the sensed eECAP signal. Therapeutic stimulation may be programmed to be delivered at a percentage of the stimulation intensity which resulted in the eECAP biomarker.

In some examples, system 22 may include an electrode patch 44, or other electrode located in an area near the target of applied stimulation. For example, electrode patch may be located in an area near the rectum when system 22 is used to treat fecal incontinence. Electrode patch 44 may collect a signal including an eECAP biomarker.

Figure 3:
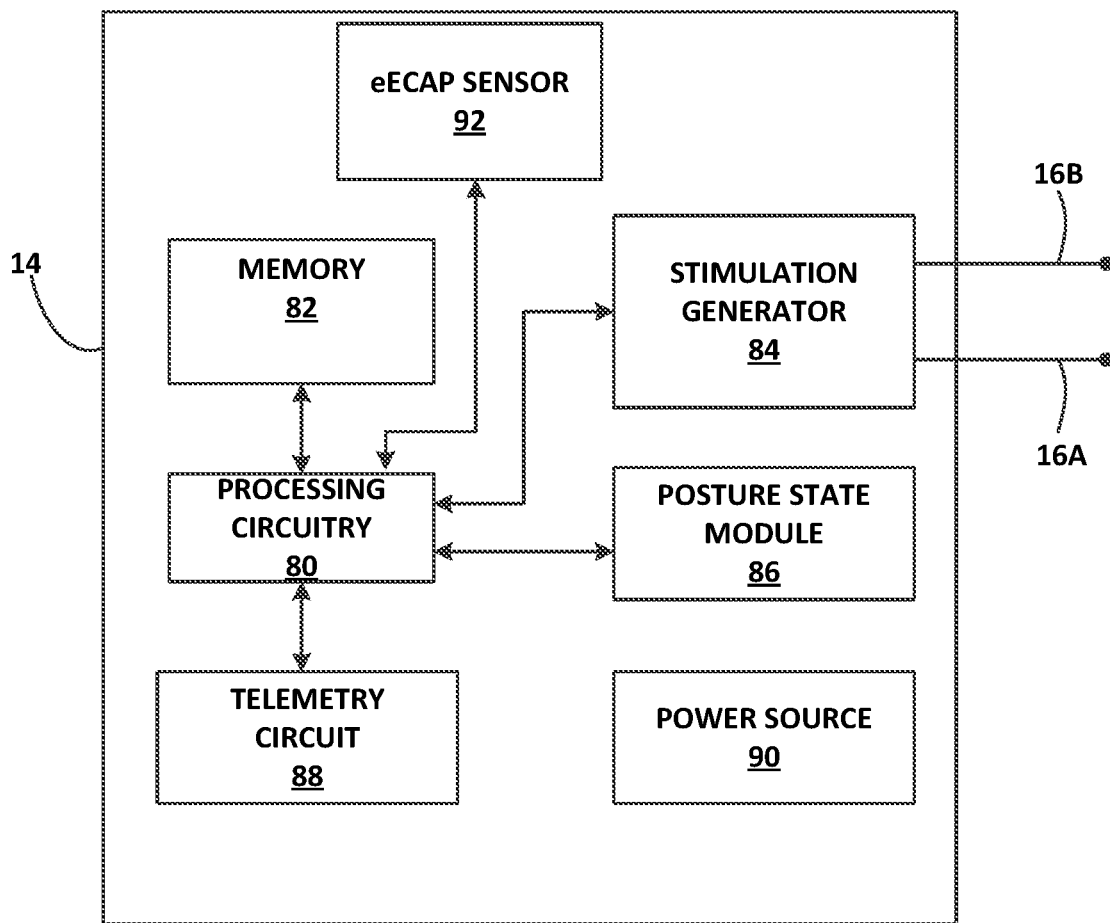
FIG. 3 is a functional block diagram illustrating example components of an IMD, such as the IMD shown in FIG. 1.

FIG. 3 is a functional block diagram illustrating various components of an IMD 14. In the example of FIG. 3, IMD 14 includes a processing circuitry 80, memory 82, stimulation generator 84, posture state module 86, telemetry circuit 88, power source 90, and eECAP sensor 92. The stimulation generator 84 forms a therapy delivery module. Memory 82 may store instructions for execution by processing circuitry 80, stimulation therapy data, eECAP biomarkers, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions including instructions for eECAP analysis, posture state information, therapy adjustment information, prior detected eECAP biomarkers, program histories, and any other pertinent data or instructions.

Processing circuitry 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processing circuitry within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processing circuitry 80. In particular, processing circuitry 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources and sinks to drive more than one electrode combination at one time. For example, each electrode may have its own current source and current sink, which can be selectively activated so that the electrode can source or sink controlled amounts of current. An electrode configuration, e.g., electrode combination and associated electrode polarities, may be represented by a data stored in a memory location, e.g., in memory 82, of IMD 14. Processing circuitry 80 may access the memory location to determine the electrode combination and control stimulation generator 84 to deliver electrical stimulation via the indicated electrode combination. To adjust electrode combinations, amplitudes, pulse rates, or pulse widths, processing circuitry 80 may command stimulation generator 84 to make the appropriate changes to therapy according to instructions within memory 82 and rewrite the memory location to indicate the changed therapy. In other examples, rather than rewriting a single memory location, processing circuitry 80 may make use of two or more memory locations.

When activating stimulation, processing circuitry 80 may access not only the memory location specifying the electrode combination but also other memory locations specifying various stimulation parameters such as voltage or current amplitude, pulse width and pulse rate. Stimulation generator 84, e.g., under control of processing circuitry 80, then makes use of the electrode combination and parameters in formulating and delivering the electrical stimulation to patient 12.

According to examples described herein, processing circuitry 80 may adjust such stimulation parameters to modify stimulation therapy delivered by IMD 14 based on the detected eECAP biomarker of patient 12. In some examples, processing circuitry 80 may detect an eECAP biomarker of patient 12 via eECAP sensor 92 that indicates that a modification of the stimulation therapy is appropriate, e.g., according to instructions stored in memory 82. Processing circuitry 80 may access instructions for modifying the stimulation therapy based on the detected eECAP biomarker, e.g., by changing from the current stimulation program to a program which results in a desired eECAP biomarker.

According to other examples described herein, such stimulation parameters may be adjusted to modify stimulation therapy delivered by IMD 14 based on a combination of the detected eECAP biomarker and a detected posture state. In some examples, processing circuitry 80 may detect an eECAP biomarker of patient 12 via eECAP sensor 92 as well as a posture state of patient 12 via posture state module 86. If a change in eECAP biomarker has been detected, a detected posture state may be used to help processing circuitry 80 determine the appropriate stimulation program in order to achieve a desired eECAP biomarker. For example, memory 82 may include a stimulation program associated with the detected posture state which resulted in the desired eECAP biomarker in the past.

An exemplary range of electrical stimulation parameters likely to be effective in treating chronic pain, e.g., when applied to spinal cord 18, are listed below. However, other parameter values are contemplated. While stimulation pulses are described, stimulation signals may be of any of a variety of forms such as sine waves or the like.

Pulse Rate: between approximately 0.5 Hz and 15 kHz, more preferably between approximately 5 Hz and 250 Hz, and still more preferably between approximately 30 Hz and 130 Hz.

Amplitude: between approximately 0.05 volts and 50 volts, more preferably between approximately 0.1 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications. Parameter values other than those described above are contemplated.

Processing circuitry 80 accesses stimulation parameters in memory 82, e.g., as programs and groups of programs. Upon selection of a particular program group, processing circuitry 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processing circuitry 80 also may control telemetry circuit 88 to send and receive information to and from external programmer 20. For example, telemetry circuit 88 may send information to and receive information from programmer 20.

In some examples, IMD 14 includes a posture state module 86 which allows IMD 14 to sense or detect the current patient posture state, e.g., posture, activity or any other static position or motion of patient 12. In the example of FIG. 2, posture state module 86 may include one or more accelerometers, such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processing circuitry 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 and/or clinician, e.g., via user interface display of external programmer 20, or some combination thereof. As an example, processing circuitry 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture state. Further, processing circuitry 80 may also adjust therapy for a new posture state when posture state module 86 indicates that patient 12 has in fact changed postures. In some examples, the change in posture may trigger sensing of eECAP. Based on the sensed eECAP from eECAP sensor 92, processing circuitry 80 may determine an appropriate adjustment to one or more current stimulation therapy parameters in order to achieve a desired eECAP biomarker. In some examples, a current eECAP biomarker may be compared to an eECAP template corresponding to efficacious therapy.

Therefore, IMD 14 may be configured to provide eECAP responsive stimulation therapy to patient 12. Stimulation adjustments in response to changes in eECAP biomarker or to patient state may be automatic or semi-automatic (subject to patient approval). In many cases, fully automatic adjustments may be desirable so that IMD 14 may react more quickly to changes in patient state, or changes in therapy efficacy that may be unrelated to a change in patient state. In some examples, eECAP sensing and analysis may be used to refine stimulation therapy programs selected based on sensed posture.

Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone or volume, processing circuitry 80 indicates that patient 12 is in the posture state of the cone or volume. In other examples, a posture state parameter value from the 3-axis accelerometer may be compared to values in a look-up table or equation to determine the posture state in which patient 12 currently resides. Examples techniques for detecting a patient posture state include examples described in U.S. Pat. No. 8,708,934, titled "REORIENTATION OF PATIENT POSTURE STATES FOR POSTURE-RESPONSIVE THERAPY," filed Apr. 30, 2009 and issued Apr. 29, 2014, the entire content of which is incorporated by reference herein.

Adjustments to one or more stimulation parameters responsive to changes in sensed eECAP may allow IMD 14 to implement a certain level of automation in therapy adjustments. In particular, IMD 14 may continuously, or on a periodic basis, adjust stimulation therapy parameters in order to maintain an eECAP biomarker that corresponds to efficacious treatment. Automatically adjusting stimulation may free patient 12 from the constant task of manually adjusting therapy each time patient 12 changes posture. Automatically adjusting stimulation based on sensed eECAP may also correct for natural drift of leads 16 irrespective of posture state. For example, by detecting eECAP biomarkers over time, processing circuitry 80 may determine that the location of the nerves being stimulated has changed over time. Such manual adjustment of stimulation parameters can be tedious, requiring patient 12 to, for example, depress one or more keys of programmer 20 multiple times during the patient posture state to maintain adequate symptom control. In some embodiments, patient 12 may eventually be able to enjoy eECAP responsive stimulation therapy, which adjusts therapy according to changing conditions without the need to continue making changes for different patient states via programmer 20. Instead, patient 12 may transition immediately or over time to fully automatic adjustments based on eECAP biomarker alone or in combination with detected patient states such as posture.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple activity sensors placed at various locations on or within the body of patient 12.

In some examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processing circuitry 80, in some embodiments, to confirm or reject changes in sensed posture state that may result from vibration, patient travel (e.g., in an aircraft, car or train), or some other false positive of posture state. In some examples, the one or more physiological parameters may be used to determine a patient state other than posture. In addition, eECAP sensing and analysis may be used to confirm a change in the relationship between the stimulation source and stimulation target within patient 12.

In addition, IMD 14 may store patient 12 input regarding perceived physiological conditions (e.g., symptoms) not detectable by any implemented sensors. For example, patient 12 may provide input to programmer 20 that indicates where the patient perceives any symptoms and characteristics of that particular type of symptom. processing circuitry 80 may associate this physiological condition information with the currently detected posture state, the stimulation parameters, and/or a time stamp to provide a complete therapy picture to the patient or clinician at a later time. Such information may be stored in memory 82 of IMD 14, the memory of programmer 20, and/or the memory of some other device.

Wireless telemetry in IMD 14 with external programmer 20, e.g., a patient programmer or a clinician programmer, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. Further, telemetry circuit 88 may transmit information, e.g., eECAP biomarker data, in real-time when communicating to an external device. For eECAP data sent in real-time, telemetry circuit 88 may send the most recently detected eECAP biomarker or a rolling average eECAP biomarker at a relative high frequency, e.g., at or near the fastest rate supported by the telemetry circuit. As described above, in some examples, raw signal information from eECAP sensor 92 may be transmitted to an external device for analysis by the external device to determine the eECAP biomarker of patient 12. To support RF communication, telemetry circuit 88 may include appropriate electronic components, such as amplifiers, filters, mixers, encoders, decoders, and the like.

When an eECAP parameter value indicates that the stimulation program administered to patient 12 has changed efficacy, processing circuitry 80 may communicate with programmer 20 via telemetry circuitry 88 to indicate the newly detected change in eECAP biomarker, i.e., a new eECAP biomarker that indicates the current efficacy of the stimulation being provided to patient 12. Alternatively, processing circuitry 80 may periodically or non-periodically send eECAP biomarker information to programmer 20 either unilaterally or in response to a request from programmer 20. For example, programmer 20 may request the most current eECAP biomarker, and transmit changes in stimulation parameter values back to 1 MB 14 based on analysis of the most current eECAP biomarker.

Power source 90 delivers operating power to the components of 1 MB 14. Power source 90 may include a small rechargeable or non-rechargeable battery and a power generation circuit to produce the operating power. Recharging may be accomplished through proximal inductive interaction between an external charger and an inductive charging coil within 1 MB 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

The eECAP sensor 92 detects eECAP signals. In some examples, eECAP sensor 92 may be located on lead 16, and may include for, example, one or more of the electrodes in leads 16 in combination with suitable amplification, filtering and/or signal processing circuitry. In some examples, eECAP sensor 92 may include additional electrode on the housing of IMD 14. In some examples, eECAP sensor 92 may be carried by an additional sensor lead positioned somewhere within patient 12, provided as an independent implantable sensor, or even worn on patient 12. For example, one or more microsensors may be implanted within patient 12 to communicate sensed eECAP biomarkers wirelessly to IMD 14. In this manner the eECAP sensed responses may be obtained independent of the location of the electrodes delivering electrical stimulation therapy.

Figure 4:
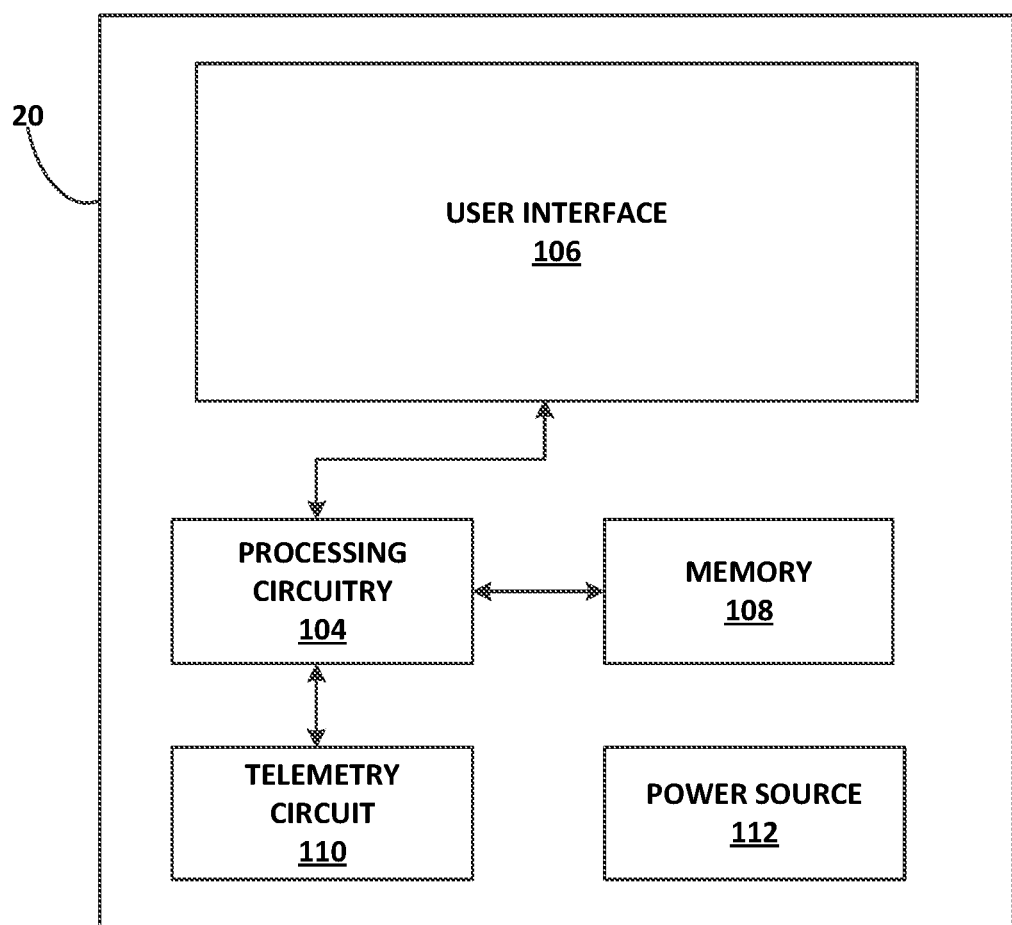
FIG. 4 is a functional block diagram illustrating example components of an external programmer for an IMD, such as the external programmer and IMD shown in FIG. 1.

FIG. 4 is a functional block diagram illustrating various components of an external programmer 20 for IMD 14. As shown in FIG. 4, external programmer 20 is an external device that includes processing circuitry 104, memory 108, telemetry circuit 110, user interface 106, and power source 112. External programmer 20 may be embodied as a patient programmer or a clinician programmer. A clinician or patient 12 interacts with user interface 106 in order to manually change the stimulation parameters of a program, change programs within a group, turn eECAP responsive stimulation ON or OFF, view therapy information, view patient state information, view a posture state indication, or otherwise communicate with IMD 14.

User interface 106 may include a screen and one or more input buttons, as in the example of a programmer, that allow external programmer 20 to receive input from a user. Alternatively, user interface 106 may additionally or only utilize a touch screen display, as in the example of a clinician programmer. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like. Input buttons for user interface 106 may include a touch pad, increase and decrease buttons, emergency shut off button, and other buttons to control the stimulation therapy, as described above with regard to programmer 20. Processing circuitry 104 controls user interface 106, retrieves data from memory 108 and stores data within memory 108. Processing circuitry 104 also controls the transmission of data through telemetry circuit 110 to IMDs 14 or 26. Memory 108 includes operation instructions for processing circuitry 104 and data related to patient 12 therapy.

Telemetry circuit 110 allows the transfer of data to and from IMD 14, or IMD 26. Telemetry circuit 110 may communicate automatically with IMD 14 in real-time, at a scheduled time, or when the telemetry circuit detects the proximity of the stimulator. User interface 106 may then update displayed information accordingly. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Figure 5:
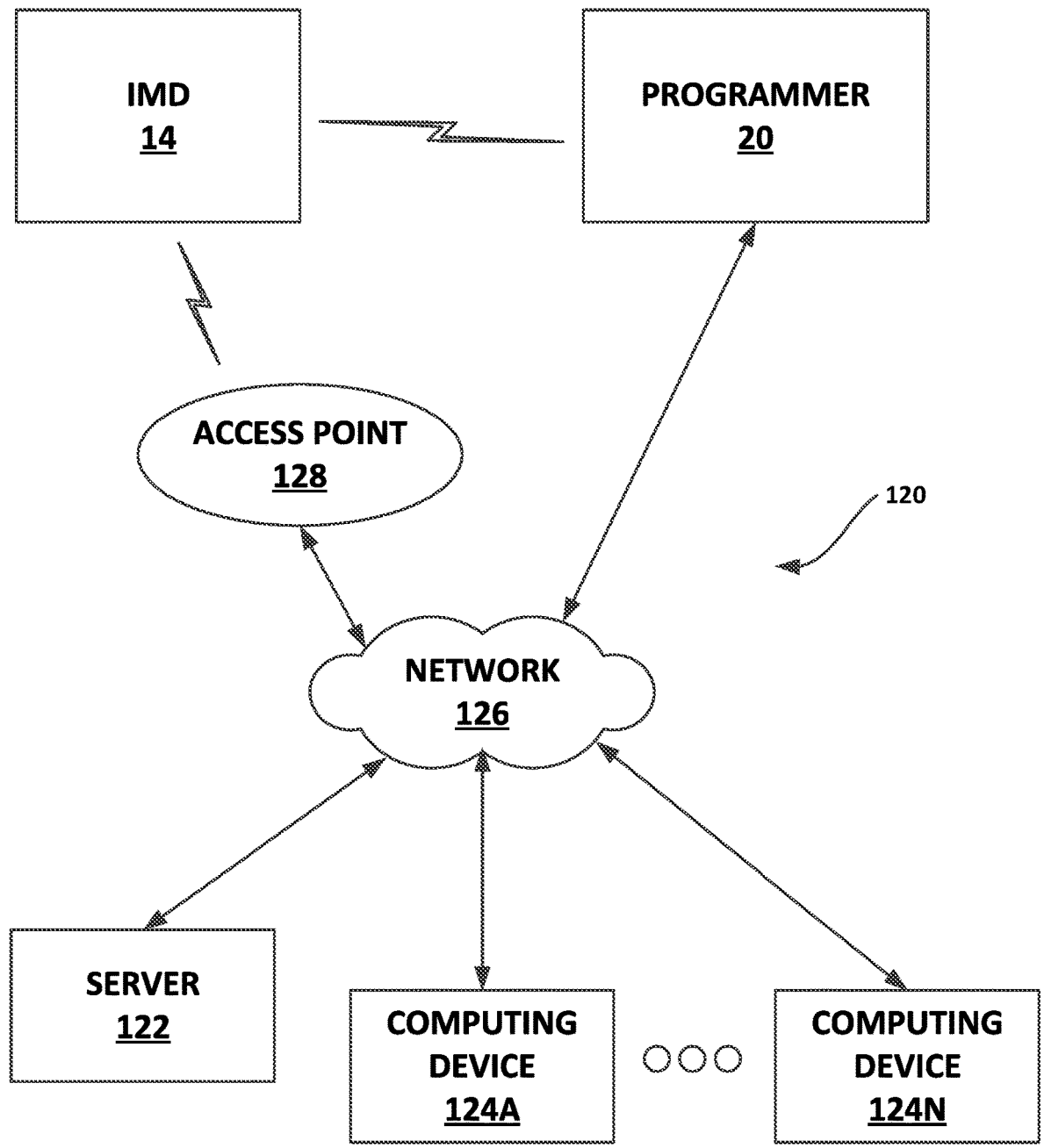
FIG. 5 is a block diagram illustrating an example system that includes an external device, such as a server, and one or more computing devices, that are coupled to IMD and external programmer shown in FIG. 1 via a network.

FIG. 5 is a block diagram illustrating an example system 120 that includes an external device, such as a server 122, and one or more computing devices 124A-124N, that are coupled to IMD 14 and external programmer 20 shown in FIG. 1 via a network 126. In this example, IMD 14 may use its telemetry circuit 88 to communicate with external programmer 20 via a first wireless connection, and to communication with an access point 128 via a second wireless connection.

In the example of FIG. 5, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed eECAP biomarkers and posture state information during therapy that indicate how patient 12 moves throughout each day, and movement of leads 16 with respect to the stimulation target. In some cases, IMD 14 may directly analyze the collected data to evaluate efficacy of adjustments to stimulation therapy based sensed patient posture. In other cases, however, IMD 14 may send stored data relating to posture state information and sensed eECAP biomarker to external programmer 20 and/or server 122, either wirelessly or via access point 128 and network 126, for remote processing and analysis.

For example, IMD 14 may sense, process, trend and evaluate the sensed eECAP response, posture state information, and other therapy information. This communication may occur in real time, and network 126 may allow a remote clinician to review the current patient posture state by receiving a presentation of a posture state indication along with other therapy information on a remote display, e.g., computing device 124A. Alternatively, processing, trending and evaluation functions may be distributed to other devices such as external programmer 20 or server 122, which are coupled to network 126. In addition, posture state information and other therapy information may be archived by any of such devices, e.g., for later retrieval and analysis by a clinician. For example, the archived therapy information may be presented to a user via user interface 106 (FIG. 3).

In some cases, IMD 14, external programmer 20 or server 122 may process posture state information, eECAP biomarker, or raw data and/or therapy information into a displayable eECAP biomarker report, which may be displayed via external programmer 20 or one of computing devices 124A-124N. The eECAP report may contain trend data for evaluation by a clinician, e.g., by visual inspection of graphic data. In some cases, the eECAP report may include the number of activities patient 12 conducted, a percentage of time patient 12 was in each posture state, how magnitude in change to the eECAP biomarker for a particular change in posture, what group or program was being used to deliver therapy during each activity, the number of manual adjustments to therapy provided in addition to eECAP responsive adjustments, or any other information relevant to patient 12 therapy, based on analysis and evaluation performed automatically by IMD 14, external programmer 20 or server 122. A clinician or other trained professional may review the historical therapy information including the stimulation parameters, physiological conditions, and changes in eECAP in response to stimulation to possibly identify any problems or issues with the therapy that should be addressed.

In addition, network 126 may be configured to facilitate real-time communication between IMD 14 and computing device 124A for programming based on a currently sensed eECAP biomarker. Although there may be some slight delay in the transfer of information, this may still be considered real-time programming utilizing any user interface such as user interfaces 200, 270, or 290. The clinician may be able to remotely visit with patient 12, review stored therapy information, and make any programming changes in real-time using system 120.

In some cases, server 122 may be configured to provide a secure storage site for archival of eECAP biomarker and patient state information that has been collected from IMD 14 and/or external programmer 20. Network 126 may comprise a local area network, wide area network, or global network, such as the Internet. In other cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve eECAP biomarkers, posture state information and related data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, programmer 20, or communicate with patient 12. In an additional example, the clinician may utilize system 120 to monitor multiple patients and share data with other clinicians in an effort to coordinate rapid evolution of effective treatment of patients. Further, eECAP biomarker detection may be used to provide notifications, such as providing notification via a wireless link to a care giver a lead has shifted substantially.

Furthermore, although the disclosure is described with respect to SCS therapy, such techniques may be applicable to IMDs that convey other therapies the relationship between lead 16 and the target stimulation location may change, such as, e.g., DBS, pelvic floor stimulation, gastric stimulation, occipital stimulation, functional electrical stimulation, and the like.

As described above, in some examples, an external device, such as, e.g., external programmer 20 may present therapy information to a user via a user interface. The therapy information presented to a user may relate to therapy delivered to a patient by IMD 14 or some other medical device. The therapy information presented by the external device may include eECAP biomarker, patient posture state information, physiological therapy information, and therapy parameter information.

The therapy parameter information and physiological therapy information may be associated with a particular eECAP biomarker. In some examples, the information may also be associated with patient posture state information. The same eECAP biomarker may be associated with more than one patient posture state. For example, the therapy parameter information presented to a user may include an indicator of one or more therapy parameters programmed for delivery for a particular eECAP biomarker or particular patient posture state indicated to the user by the user interface. In some examples, the therapy parameter information may include an indicator of previous adjustments made by a user to one or more therapy parameters for therapy delivered to a patient in order to achieve a desired eECAP biomarker associated with efficacious therapy. In the case of physiological condition information, physiological conditions associated with patient posture state information may include physiological symptoms experienced by the patient when in a particular posture state.

The user interface of an external device may be configured to receive feedback from a user (e.g., a patient or clinician) regarding physiological conditions information and/or the therapy parameter information associated with patient posture state information. In one example, the external device including the user interface for presenting therapy information may receive one or more therapy parameters for the therapy associated with a specific posture state of the patient. Such therapy parameter adjustments may be communicated to IMD 14 or other device for delivering therapy to patient 12 for the associated posture state. In another example, the external device including the user interface for presenting the therapy information may receive input regarding one or more physiological conditions indicated by a patient for a particular posture state. The therapy information presented to a user may be updated based on the input received from a user via the user interface.

Figure 6:
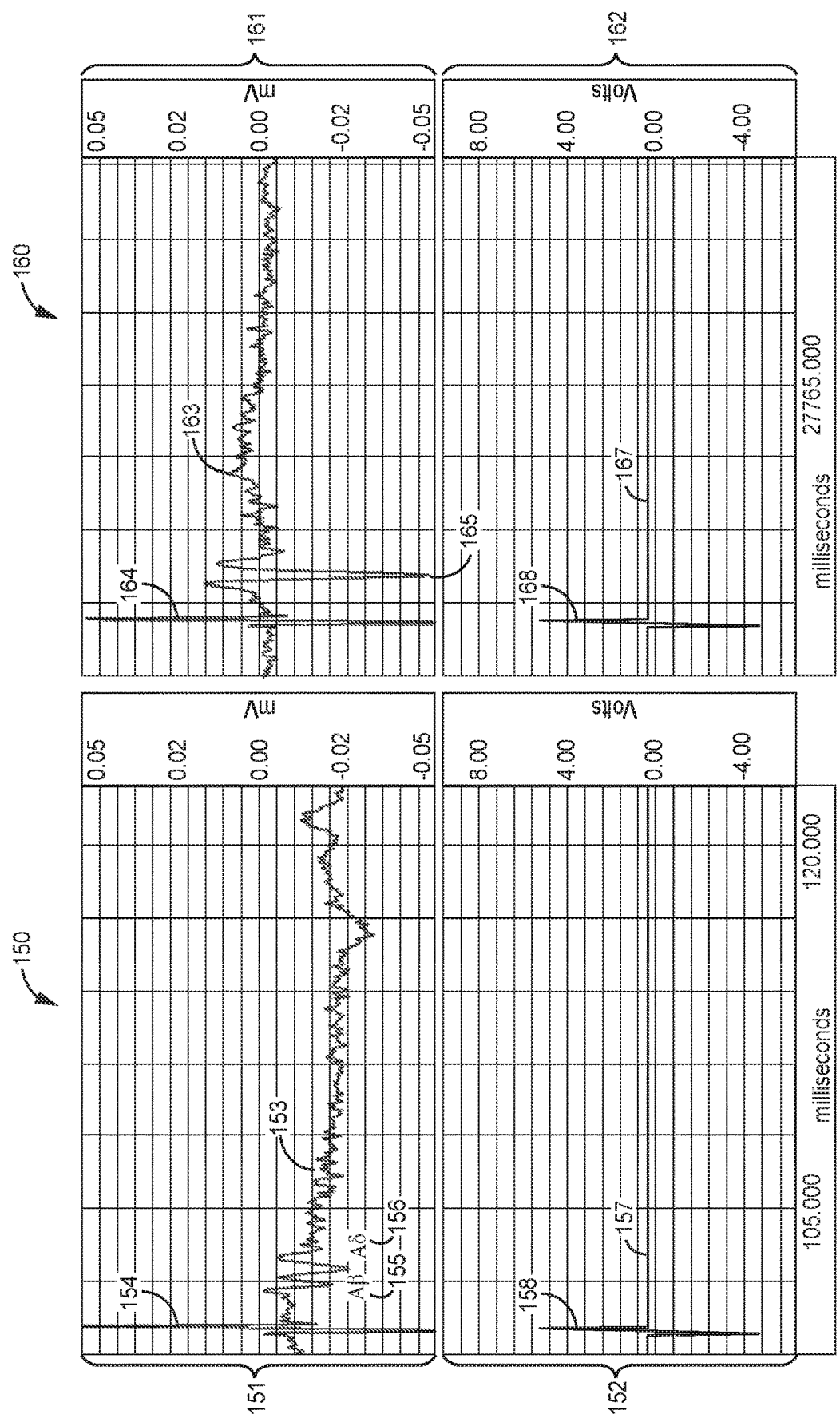
FIG. 6 illustrates a pair of graphs, each graph illustrating a stimulation pulse, and the sensed eECAP signal generated in response to the stimulation pulse, respectively.

FIG. 6 illustrates a pair of graphs 150, 160, each graph illustrating a stimulation pulse, and the sensed eECAP signal generated in response to the stimulation pulse, respectively. Prior to the collection of the traces shown in graphs 150 and 160, the lumbar spine being monitored for the eECAP signal was bursted with stimulation therapy provided at a frequency of 10 kHz for one minute. Recording of the eECAP is not feasible during the 10 kHz high frequency burst owing to stimulation artifacts obscuring the neural response. A slower stimulation frequency, in this case, a 10 Hz stimulation pulse, provides ample opportunity to generate the eECAP after the slower frequency stimulation pulse is delivered with no corruption from the stimulation artifact. Although 10 Hz was used to elicit the eECAP in this particular example, other frequencies both faster and slower such as those between about 1 Hz and 500 Hz, between 2 Hz and 250 Hz and about 50 Hz are also contemplated for use in providing low frequency stimulation.

As illustrated in graph 150, an electrical stimulation signal 157 including a stimulation pulse 158, as generally indicated by bracket 152, is applied to the spine of a sheep (test patient) with a Medtronic Model 3778 1×8 Compact Percutaneous Lead. The electrical stimulation signal 157 comprises a stimulation pulse having parameters of 5V biphasic, applied at frequency of 10 Hz for 60 µs, delivered with a Medtronic Model 39565 lead in the mid-lumbar spine. The stimulation pulse 158 is delivered 0.1 seconds after cessation of the 10 kHz high frequency burst and in this example is delivered continuously for a time period after cessation of the high frequency stimulation. The eECAP signal 153 sensed in response to the stimulation pulse 158 is generally indicated by bracket 151. The sensed eECAP signal 153 includes a pulse 154 that was sensed during a time when the stimulation pulse 158 was being applied to the test patient. The sensed eECAP signal also includes a first peak 155 attributed to nerve firing of the Aα Type I fibers, and a second (later in time) peak 156 attributed to nerve firing of Aα Type II fibers.

As illustrated in graph 160, an electrical stimulation signal 167 incudes a stimulation pulse 168, as generally indicated by bracket 162, is applied to the spine of the sheep (test patient) in a same manner as described above, using the same parameters (5V biphasic, applied at frequency of 10 Hz for 60 µs), and using the same lead and same sensing electrodes as described above for electrical stimulation signal 157, except that stimulation signal 167 is applied 27 seconds after cessation of the 10 kHz stimulation instead of the 0.1 second delay used in the application of stimulation signal 157. The eECAP signal 163 sensed in response to the stimulation pulse 168 is generally indicated by bracket 161. The sensed eECAP signal 163 includes a pulse 164 that was sensed during a time when the stimulation pulse 168 was being applied to the test patient. The sensed eECAP signal also includes a peak 165. As illustrated by eECAP signal 163, the effect of the high-frequency stimulation (10 kHz one-minute burst) has washed out, and only a single peak is evident in the eECAP associated with nerve firing of the Aα Type I fibers, wherein any contribution to the eECAP signal generated by the nerve firing of Aα Type II fibers is masked by the much larger Aα Type I eECAP. In some examples, the level of stimulation provided by pules 158, 168 may be below the level that is perceptible to a patient, such as a human patient. In other examples, the level of stimulation provided by pulses 158, 168 is above the level that is perceptible to a patient, such as a human patient. The peak amplitudes of the Aα Type I and Type II eECAP signals after cessation of the 10 kHz burst as a function of time are further illustrated and described below with respect to FIG. 7. Although shown as a "ping" or a pulse in FIG. 6, the low frequency stimulation may be delivered continuously beginning immediately after cessation of the application of the high frequency burst, and delivered for some predefined period of time, such as 30 seconds. During the time of application of the low frequency stimulation, the eECAP is capable of being measured, either continuously, or at some predetermined sample rate, to sense the eECAP signals referred to herein.

Figure 7:
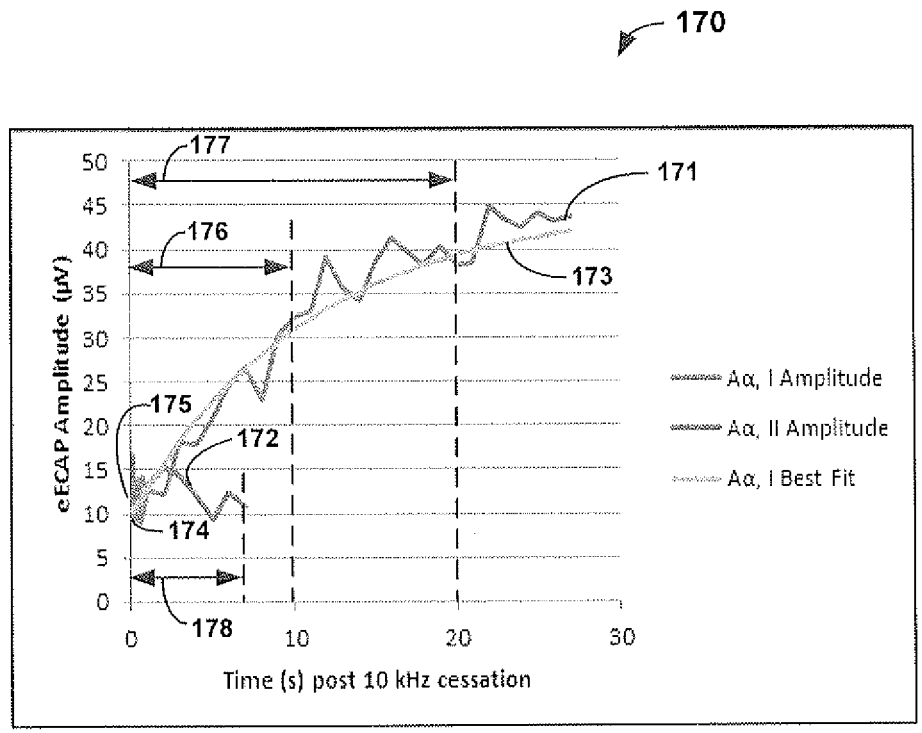
FIG. 7 illustrates a graph of peak amplitudes of eECAP from nerve fibers after cessation of an applied burst of electrical stimulation in accordance with various techniques consistent with this disclosure.

FIG. 7 illustrates a graph 170 of peak amplitudes of an eECAP signal for Aα Type I nerve fibers and for Aα Type II nerve fibers after cessation of an applied burst of electrical stimulation as a function of time. The applied burst of electrical stimulation is a same 10 kHz burst of stimulation, applied to the spine of the sheep (test patient) is the manner described above with respect to FIG. 6. The plot of the eECAP for both the Aα Type I nerve fibers and for Aα Type II nerve fibers as shown in FIG. 7 is derived from plots from the eECAP signals 153 and 163 as illustrated and described above with respect to FIG. 6.

As shown in FIG. 7, graph 170 comprises a vertical axis representing the eECAP amplitude of the signals in volts, and a horizontal axis representing time in seconds after cessation of the 10 kHz therapy signal. The zero-point origin along the horizontal axis of graph 170 represents the time of cessation of the 10 kHz stimulation, and the time to the right along the horizontal axis represents the number of seconds following the cessation of the 10 kHz stimulation burst. Graph 170 includes a trace 171 illustrating the peak amplitudes of the eECAP signal associated with the Aα Type I nerve fibers following cessation of the 10 kHz burst, and a trace 172 illustrating the peak amplitudes of the eECAP signal associated with the Aα Type II nerve fibers following cessation of the same 10 kHz burst. Graph 170 also illustrates a trace 173 representative of a least squares fit to the Aα Type I data of trace 171 of the form OFFSET+(eECAP Initial Value)*(1−e^(−t/τ)). While the eECAP amplitude was assessed for each of the fiber types in graph 170, other assessments of the eECAP signal associated with the integral, power, or area under the curve could be used interchangeably for analysis of the eECAP traces and for comparison purposes between the signals associated with the Aα Type I and the Aα Type II nerve fibers.

As illustrated in FIG. 7, the amplitude (i.e., the magnitude of the voltage) represented by the vertical axis of graph 170 represents the level of nerve firing provided by the respective nerve fibers to a patient's brain. The higher the voltage level of the trace, the more nerve firings, and in general the more indication of a sensation of pain is being sent through the spinal column of the patient. The application of the 10 kHz burst of stimulation therapy may be intended to drive down the amplitudes (level of nerve firing activity) being sent through the spinal column, and modulate the perception of pain experienced by the patient receiving the stimulation therapy. As shown in Graph 170, at the time of cessation of the 10 kHz burst of stimulation, the amplitude of the eECAP signals for the Aα Type I nerve fibers has an initial value 174 at time zero of approximately 10 µV. The amplitude of the eECAP signal associated with the Aα Type II nerve fibers has nearly a same or slightly higher initial value 175. As shown by trace 172, the amplitude value of the eECAP associated with the Aα Type II nerve fibers varies between approximately 15 and 9 µV, wherein the masking of the Aα Type II eECAP is complete in a time period 178 of about eight seconds after the 10 kHz burst terminates. As shown by trace 171, the amplitude value of the eECAP associated with the Aα Type I nerve fibers begins at an initial (offset) value of approximately 10 µV, but in view of the fitted curve of trace 173, increases in magnitude after cessation of the 10 kHz burst in somewhat of an exponential-shaped curve. After a first time period 176 following cessation of the 10 kHz burst, (i.e., 10 seconds), the amplitude of fitted trace 173 has risen to a value just over 30 µV, and after a second time period 177 following cessation of the 10 kHz stimulation (i.e., 20 seconds), the amplitude of the fitted trace 173 has continued to rise to a value just under 40 µV.

Based on the traces 153, 163 of the eECAP signals as provided in FIG. 6, and/or the plots of the eECAP amplitudes represented by traces 171, 172, 173 shown in FIG. 7, various parameters may be directly measured from these traces, and/or derived from measurements taken from these traces, or other types of traces the could be derived from the eECAP signals as mentioned above. Example parameters of interest which may be extracted from the eECAP following a specific therapeutic or diagnostic intervention may include, but are not limited to:

Fiber latency (relative to the stimulation pulse)—in some examples represented by a time between stimulation pulse and the peak of the resulting eECAP signal.

Time to specific fiber type masking—in some examples the time may be determined when a particular ratio is achieved between the value of one eECAP signal generated by a particular type of nerve fiber exceeds a threshold ratio of an eECAP signal generated by a different particular type of nerve fiber eECAP width—in some examples, a width (in time) of some portion of an eECAP signal bounded by some redeemed threshold values for the waveform eECAP amplitude, area under the curve, power or integral offset eECAP amplitude, area under the curve, power or integral initial value eECAP recovery time constant Also additional parameters may be derived parameters based on the eECAP signals such as but not limited to:

Ratio of eECAP amplitude, area under the curve, or power for one fiber type versus that of another.

Difference in fiber latency for one fiber type with respect to another.

As further described below, one or a combination of these parameters may be used to compare one sensed eECAP signal to another eECAP signal, or to compare a sensed eECAP signal to a target eECAP for the purposes of evaluating the applied stimulation therapies that generated the eECAP signal against one another. Thus, the eECAP signal and the associated parameters of the eECAP signals provide a tool to determine relative efficacies of the stimulation therapies for a patient, and/or relative system performance features of the systems providing the stimulation therapies, such as IMD 14, while providing stimulation therapies based on different therapy parameters.

For example, the initial value 174 for the Aα Type I nerve fibers of approximately 10 µV may be used as a baseline value for this eECAP parameter. Another eECAP signal may be are sensed that was generated by applying a candidate therapy, the candidate therapy utilizing a set of therapy parameters that was different in at least one therapy parameter value than was used in the stimulation therapy that generated the baseline eECAP. By comparing the initial value measured for the Aα Type I nerve fiber response of the candidate therapy to the initial value 174 of the baseline eECAP, a determination can be made as to whether the eECAP generated by the candidate therapy is different from or is equivalent to the baseline eECAP. For example, the eECAP generated by the candidate therapy may be considered "different from" the baseline eECAP if the initial value measured for the eECAP generated by the candidate therapy exceeds the initial value 174, (e.g., exceeds 10 µV), and may be considered "equivalent to" the baseline eECAP if the initial value for the eECAP generated by the candidate therapy is less than or equal to the initial value 174 of the baseline eECAP.

In another example, the eECAP generated by the candidate therapy may be considered to "match" to a target eECAP if the initial value measured for the eECAP generated by the candidate therapy falls within a range of values that includes or is based on initial value 174. For example, if a measured initial value of the eECAP for the Aα Type 1 nerve fibers generated by the candidate therapy is measured and is determined to fall within ±0.5V of the initial value 174 determined for the baseline eECAP, then the eECAP signal associated with the candidate therapy may be considered to be a "match" for the baseline eECAP. Comparisons of the initial values as described above are not limited to an initial value associated with a particular type of nerve fiber, and may be performed with respect to any type of nerve fiber generating an eECAP response, and the comparisons in some examples is made between corresponding initial values for two or more different nerve fiber types to determine whether the eECAP signals are different or equivalent of one another and/or are a match to a target eECAP.

In another example of eECAP signal parameters that may be used to compare a baseline eECAP signal to an eECAP generated by a candidate therapy, a measured value at some predetermined time following cessation of the 10 kHz stimulation, or cessation of some other stimulation therapy, may be compared. For example, as shown in graph 170 a value of the eECAP signal after time period 176 of 10 seconds is approximately 30.5 µV. This value can be stored as a baseline value for this eECAP parameter, and a corresponding measurement at the 10-second mark can be taken from an eECAP signal generated in response to an applied candidate therapy. The value of the eECAP generated in response to the candidate therapy at the 10-second mark can be compared to the baseline 30.5 µV value, or to a range of values determined based on the 30.5 µV baseline value. Based on that comparison, a determination can be made as to whether the eECAP generated in response to the candidate therapy is different from or equivalent to the baseline eECAP, or for example is a "match" to the baseline eECAP. The time period used for the measurement of the eECAP value is not limited to any particular time frame, and for example may be a different time period 177 comprising a 20 second time period. In some examples, comparison of more than one set of values measured after predetermined time period 176, 177 may be used to compare eECAP generated by the candidate therapy to the baseline eECAP.

In another example of a parameter that may be used to compare eECAP signals, change in the value of the eECAP signal over a predetermined time period may be used. For example, the difference between the value of the eECAP signal at the end of time period 176 may be subtracted from the value of the eECAP signal at the end of time period 177 to generated a delta (change in value) parameter for the eECAP signal over the period of time between the end of time period 176 and the end of time period 177. For example, the value of the eECAP signal as shown in graph 170 at the end of time period 177 is approximately 39.5 µV, and the value at the end of time period 176 is approximately 30.5 µV. The delta value is therefore calculated to be approximately 9.0 µV. This 9.0 µV value may be used as the baseline value for this parameter, and the eECAP signal generated of the candidate therapy may be analyzed to determine the delta value for this parameter of the eECAP as generated by the candidate therapy. The generated delta value for the eECAP signal of the candidate therapy may be compared to the baseline value for this same parameter, as described above, to determine whether the eECAP signal is different from or equivalent to, and/or is a match for the baseline eECAP.

In another example of a parameter that may be measured from the graph 170, a time period 178 can be taken relative to trace 172, time period 178 a measurement of the time from cessation of the 10 kHz burst until the masking of the eECAP signal represented by nerve firing of the Aα Type II nerve fibers. The value determined for time period 178 is an example of a parameter that may be used to classify the eECAP signal that provided trace 172. For example, the value determined for time period 178 can be compared to the value for this same eECAP signal determined for a baseline eECAP signal, and if the value of time period 178 is within a predefined range of values for this same parameter of the baseline, the signal represented by trace 172 may be classified as a match, or as equivalent to (i.e., is not different from) the baseline signal. In an alternate example, the value of this same parameter for the baseline may be considered to be a threshold values, and for example the signal represented by trace 172 may be classified as either exceeding this threshold (e.g., time period 178 is greater than the time period corresponding to this same parameter for the baseline signal) if the value of time period 178 exceed the value of the baseline signal, or not exceeding this threshold (e.g., time period 178 is less than the time period corresponding to this same parameter for the baseline signal) if the value of time period 178 does not exceed this threshold value of the baseline signal. If the value of time period 178 for a particular eECAP signal does not exceed the value for this parameter of the baseline signal, the eECAP associated with the candidate therapy is classified as being equivalent to the baseline signal, and if the value of time period for the particular eECAP signal does exceed the value of this parameter for the baseline signal, the particular eECAP signal is classified as different from the baseline. Thus, the value measured for time period 178 is an example of a parameter associated with an eECAP signal that may be used to classified the eECAP response associated with the signal.

As would be understood by one of ordinary skill in the art, the above provided examples of parameters used to compare eECAP signals are illustration, and intended to be non-limiting examples. Many other possibilities exist for parameters that may be either directly measured from or derived from an eECAP signal, and are contemplated for use by the systems, devices, and method described in this disclosure for use in comparing eECAP signals. In addition, use of parameters associated with eECAP signals for comparison of eECAP signals is not limited to use of a single parameter in making the determination that two or more eECAP signal may be different or equivalent to each other, or are a match when compared to each other. In various examples, multiple parameters may be compared between different eECAP signals in making these determinations related to equivalency or/and matching between eECAP signals. Additional examples of various parameters that may be determined using analysis of parameters associated with eECAP signal(s) are illustrated with respect to FIG. 8.

Figure 8:
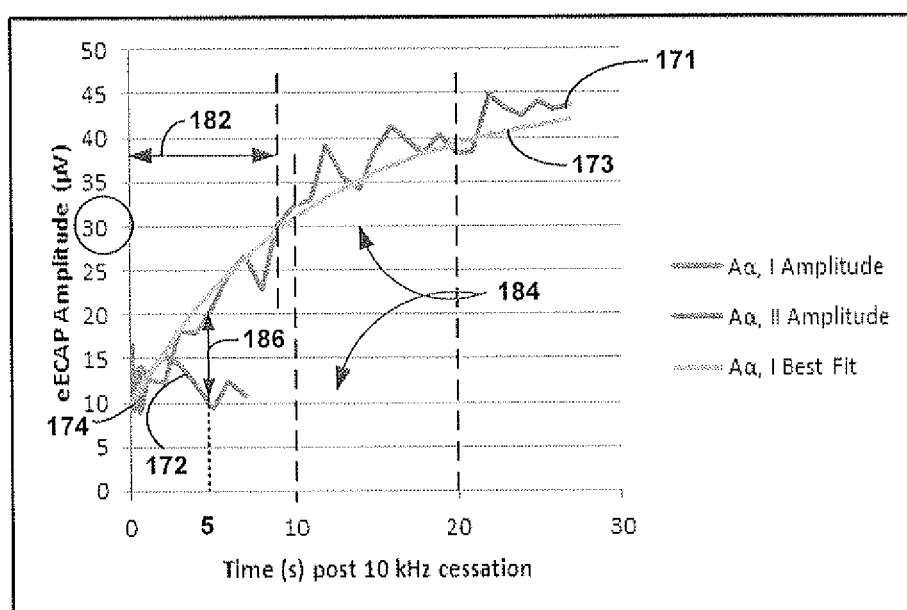
FIG. 8 illustrates a graph showing various measurements taken directly from and derived from eECAP from nerve fibers after cessation of an applied burst of electrical stimulation in accordance with various techniques consistent with this disclosure.

FIG. 8 illustrates a graph 180 showing various measurements taken directly from and derived from eECAP signals generated by nerve fibers after cessation of an applied burst of electrical stimulation in accordance with various techniques consistent with this disclosure. In a same manner as illustrated in graph 170 of FIG. 7, graph 180 of FIG. 8 illustrates trace 171 illustrating the peak amplitudes of the eECAP signal associated with the Aα Type I nerve fibers following cessation of the 10 kHz burst, and trace 172 illustrating the peak amplitudes of the eECAP signal associated with the Aα Type II nerve fibers following cessation of the same 10 kHz burst. Graph 180 also illustrates a trace 173 representative of a least squares fit to the Aα Type I data of trace 171. Graph 180 is further illustrative of examples of parameters associated with the eECAP signals and traces that may be used to classify the eECAP signals.

As illustrated in graph 180, a time period 182 can be measured that indicates a time period between the cessation of the 10 kHz burst and the time when the amplitude value of the eECAP signal for the Aα Type 1 nerve fibers reaches a predetermined value. By way of example, a value of 30 µV (circled in graph 180), is used as the predetermined amplitude value for determining this parameter. The time period 182 of approximately 9 seconds is measured as value (length) for the time period between cessation of the 10 kHz burst and the time when the value of the amplitude of the eECAP associated with the Aα Type I nerve fibers reaches a value of 30 µV, which corresponds to the predetermined amplitude value. The length of time period 182 may be used as a baseline value for this parameter, and the corresponding parameter value as measured for one or more eECAP signals measured in response to the application of candidate therapies may be used to determine if the eECAP generated by the candidate therapy is different from or equivalent to, and/or is a match for the baseline eECAP. In various examples, the predetermined value may be useful in that the value determines a threshold level where a patient may begin to feel a pain sensation based on the level of nerve firing, and where another stimulation therapy may need to be applied to again drive down the amplitude of the level of the signal being generated by the nerve fibers.

In another example of a eECAP signal parameters as shown in graph 180, an area 184 below trace 171 or trace 173 that is bounded by a first predetermined time (e.g., 10 seconds) and a second predetermined later time (e.g., 20 seconds) following cessation of the 10 kHz burst may be calculated to determine a parameter associated with the eECAP signal corresponding to trace 171 or 173. This calculated parameter may be used to classify the eECAP signal against a baseline (e.g., is different from or equivalent to baseline), or to determine if the eECAP signal sensed to generate trace 171 or 173 is a match for a predefined eECAP signal by comparison of the value of area 184 to the corresponding area value calculated for the predefined eECAP signal. Thus, the value calculated for area 184 is another example of a parameter associated with an eECAP signal that may be used to classified the eECAP responses.

In another example of an eECAP signal parameters that may be used to classify eECAP signals, a difference value 186 may be determined for the difference in amplitude values for the Aα Type I and the Aα Type II nerve fibers at one or more predetermined times after cessation of the 10 kHz burst. As illustrated in graph 180, a difference value between the amplitude of trace 172, representative of the amplitude value of the Aα Type II nerve fibers, and the amplitude of trace 171, representative of the amplitude value of the Aα Type I nerve fibers, may be measured at some predetermined time, e.g., 5 seconds after cessation of the 10 kHz burst. The difference values 186 may be stored as a baseline value, and used to compare with the corresponding values measured for other eECAP signals generated in response to application of a candidate therapy to determine whether the eECAP generated by the candidate therapy is different from, equivalent to, and/or is a match for the baseline eECAP, as described above with respect to other eECAP parameters. Measurement of difference value 186 is not limited to being taken at any particular time period following cessation of the 10 kHz bust, and is not limited to only include a signal difference value taken at one particular time. In some examples, multiple measurements of the difference value between the signals may be taken at different times, respectively. In some examples, each of these measured difference values may be used as an individual eECAP parameter for comparing eECAP signals. In other examples, multiple measurements of the difference values for a given set of eECAP signals associated with a same stimulation therapy may be combined, for example added together and averaged, to form a single overall difference value for that eECAP. This overall difference value may then be used as an eECAP parameter for comparing a baseline eECAP signal to one or more eECAP signals generated by the application of candidate therapies to a patient. These examples of eECAP parameters, as illustrated by graph 180, are intended to be non-limiting illustrative examples, and in no way limit the number and types of parameters that are contemplated for use by the systems, devices, and methods of the present disclosure for use in in comparing eECAP signals.

Figure 9:
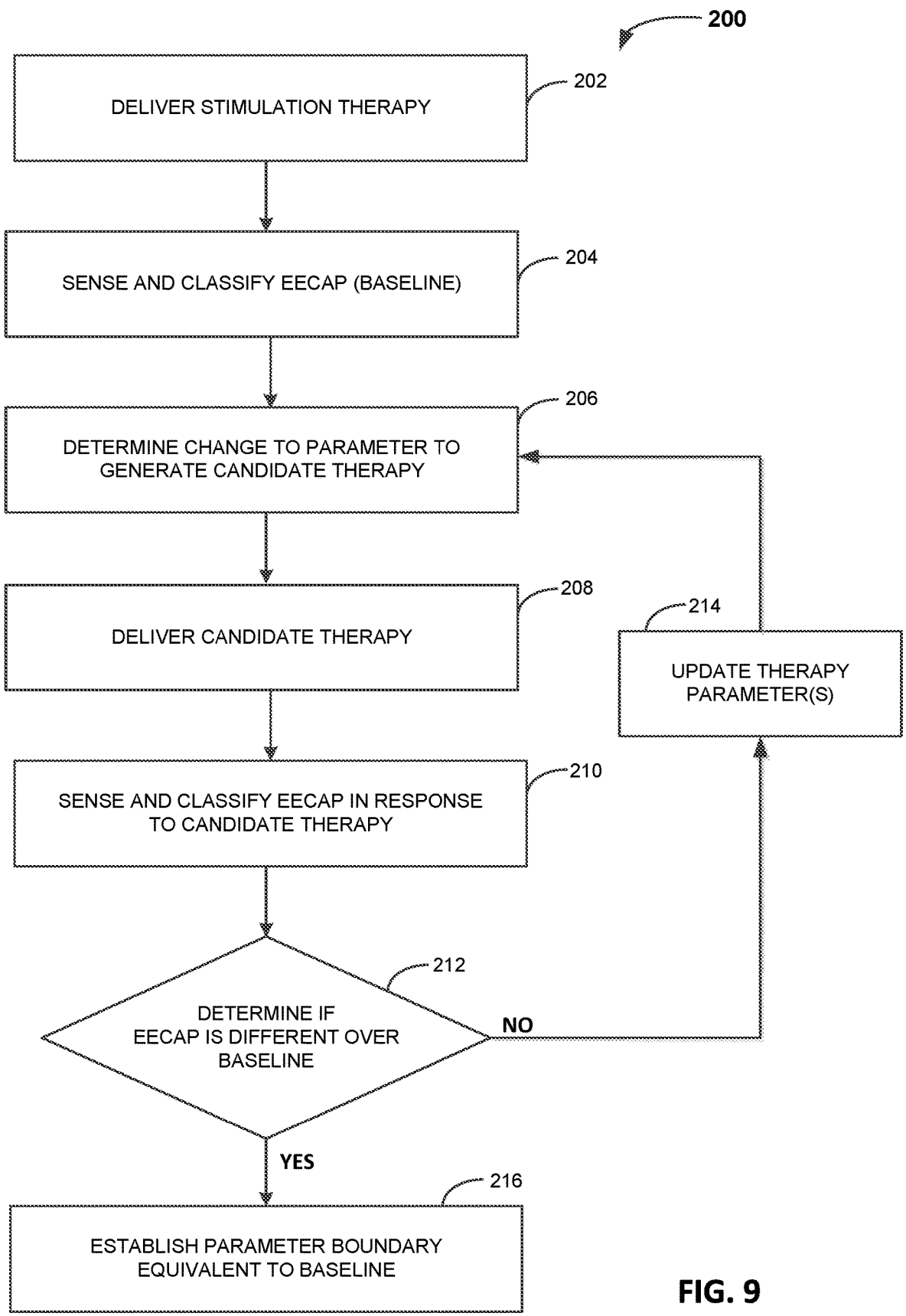
FIG. 9 is a flow diagram illustrating an example method for adjusting electrical stimulation therapy parameters based on a sensed eECAP in response to applied stimulation in accordance with various techniques consistent with this disclosure.

FIG. 9 is a flow diagram illustrating an example method 200 for adjusting electrical stimulation therapy parameters based on sensed eECAP signals in response to applied stimulation in accordance with various techniques consistent with this disclosure. Although discussed with respect to IMD 14 of FIG. 1, the method 200 of FIG. 9 may be implemented, in whole or in part, by system 22 of FIG. 2, and may be implemented, in whole or in part, by system 120 of FIG. 5. In various examples, method 200 may be performed in whole or in part by any of the processing circuitry described herein. In various examples, it may be desirable to influence the dynamics of the dorsal column in an equivalent manner that was achieved with a particular stimulation therapy, for example using a 10 kHz stimulation burst, but using a stimulation therapy with a different set of therapy parameters, for examples a stimulation therapy provided at a lower frequency. Using the frequency example for therapy parameters, this may be done by adapting the SCS frequency until the characterized eECAP no longer matches the initial characterization achieved when using the higher frequency stimulation therapy. The approach is useful for defining the parameter limits (e.g., the "metes and bounds") over which alternative therapy parameters can be used to provide an equivalent therapy result relative to a baseline result but using a different set of therapy parameters. The alternative therapy may provide an equivalent level of therapy efficacy, but provide one or more system performance advantages over the use of the original therapy parameters.

As illustrated, in method 200 IMD 14 delivers electrical stimulation as a therapeutic or a diagnostic intervention (stimulation therapy) to a patient (block 202). IMD 14 senses an eECAP signal generated by one or more nerve fiber bundles in response to the delivered electrical stimulation, and classifies the sensed eECAP signal as a baseline (block 204). Classification of the sensed eECAP signal may comprise measurement and/or derivation of any type of parameter associated with the sensed eECAP signal. IMD 14, e.g., processing circuitry 80 of IMD 14, determines a change to a parameter that is used to generate a candidate therapy, the candidate therapy different from the therapeutic/diagnostic intervention stimulation that resulted in the sensed eECAP baseline signal (block 206). In some examples, the change in a parameter comprises lowering the frequency parameter of the electrical stimulation used in the candidate therapy relative to the frequency of the electrical stimulation used in the therapeutic/diagnostic intervention therapy. In some examples, lowering the frequency comprises lowering the frequency by some predetermined and incremental amount. In some examples, a change in parameters may be determined based at least in part when there has been a detected change in activity level or posture of the patient. IMD 14 then delivers the candidate therapy based on the generated candidate therapy parameters (block 208). IMD 14 senses an eECAP signal generated by the one or more nerve fiber bundles in response to the delivered candidate therapy, and classifies the sensed eECAP signal (block 210). Classification of the sensed eECAP signal may comprise measurement and/or derivation of any type of parameter associated with the sensed eECAP signal, and comparison of these parameters to the corresponding parameters associated with the eECAP baseline.

IMD 14 determines if the sensed eECAP signal generated in response to the candidate therapy is different over the baseline (block 212). If IMD 14 determines that the sensed eECAP signal generated in response to the candidate therapy is not different over the baseline eECAP signal, (a "NO" output is generated at block 212), the process of method 200 moves to block 214. At block 214, IMD 14 updates the therapy parameter that was initially changed at block 206. Updating the therapy parameter in some examples includes a further incremental adjustment of the value of the therapy parameter relative to the value used for that parameter in the last applied candidate therapy. In some examples, an update in parameters may be determined based at least in part on when there has been a detected change in activity level or posture of the patient. The further updated therapy parameter is then provided to block 206, wherein IMD 14 uses the updated therapy parameter to generate a new candidate therapy using the updated parameter. The candidate therapy generated using the updated parameter is delivered to the patient (block 208).

IMD 14 again senses the eECAP signal generated by the one or more nerve fiber bundles in response to the delivered candidate therapy, and again classifies the sensed eECAP signal (block 210). Again, IMD 14 determines if the sensed eECAP signal generated in response to the candidate therapy including the most recently updated parameter is different over the baseline (block 212). If IMD 14 again determines that the sensed eECAP signal generated in response to the candidate therapy is not different over the baseline eECAP signal, (a "NO" output is generated at block 212), and the process of method 200 moves again back to block 214 to again update the therapy parameter. In various examples of method 200, the number of times the therapy parameter is updated and a new candidate therapy is generated and delivered based on the updated therapy parameter is not limited to any particular number of iterations. In some examples, the process of updating therapy parameters, generating and delivering candidate therapy based the update to the therapy parameter, sensing and classifying the eECAP signal that occurred in response to the candidate therapy, and determining if the eECAP signal is different from the baseline can be performed until a "YES" output is generated at block 212.

In various examples, a "YES" output is generated by IMD 14 when IMD 14 determines that a sensed and categorized eECAP signal generated in response to any of the candidate therapies is different over (i.e., is not equivalent to) the baseline. When the "YES" output decision is determined at block 212, method 200 proceeds to block 216, wherein IMD 14 establishes a parameter boundary for the therapy parameter that provides an eECAP signal equivalent to the baseline. In various examples, the parameter boundary for the therapy parameter is established as the last therapy parameter that was used to generate a candidate therapy that was applied to the patient and resulted in a sensed and categorized eECAP signal that was not different from the baseline.

By using process of method 200, a therapy parameter associated with the delivery of stimulation therapy can be changed, for example incrementally, and delivered as a candidate therapy. The sensed eECAP signal the results from the delivery of the candidate therapy can be compared to one or more aspects and/or one or more parameters associated with a baseline eECAP signal, to determine if the candidate therapy can be used to generate an equivalent eECAP signal response as generated by the baseline therapy, and thus provide a same or substantially equivalent therapy treatment, but using different therapy parameter that may provide a performance or other advantage over the baseline therapy. Examples of such an advantage would be a longer battery life for IMD 14, or for example less exposure of the patient to higher frequency or stronger electrical fields associated with applied stimulation therapy. By using the iterative process described by method 200, a parameter boundary associated with a therapy parameter, such as a lower limit, can be determined for the therapy parameter that, when incorporated into a stimulation therapy and delivered to a patient, may provide a same level of efficacy of treatment, but with one or more benefits and advantages over operations with the therapy parameter not set at the therapy parameter boundary.

Figure 10:
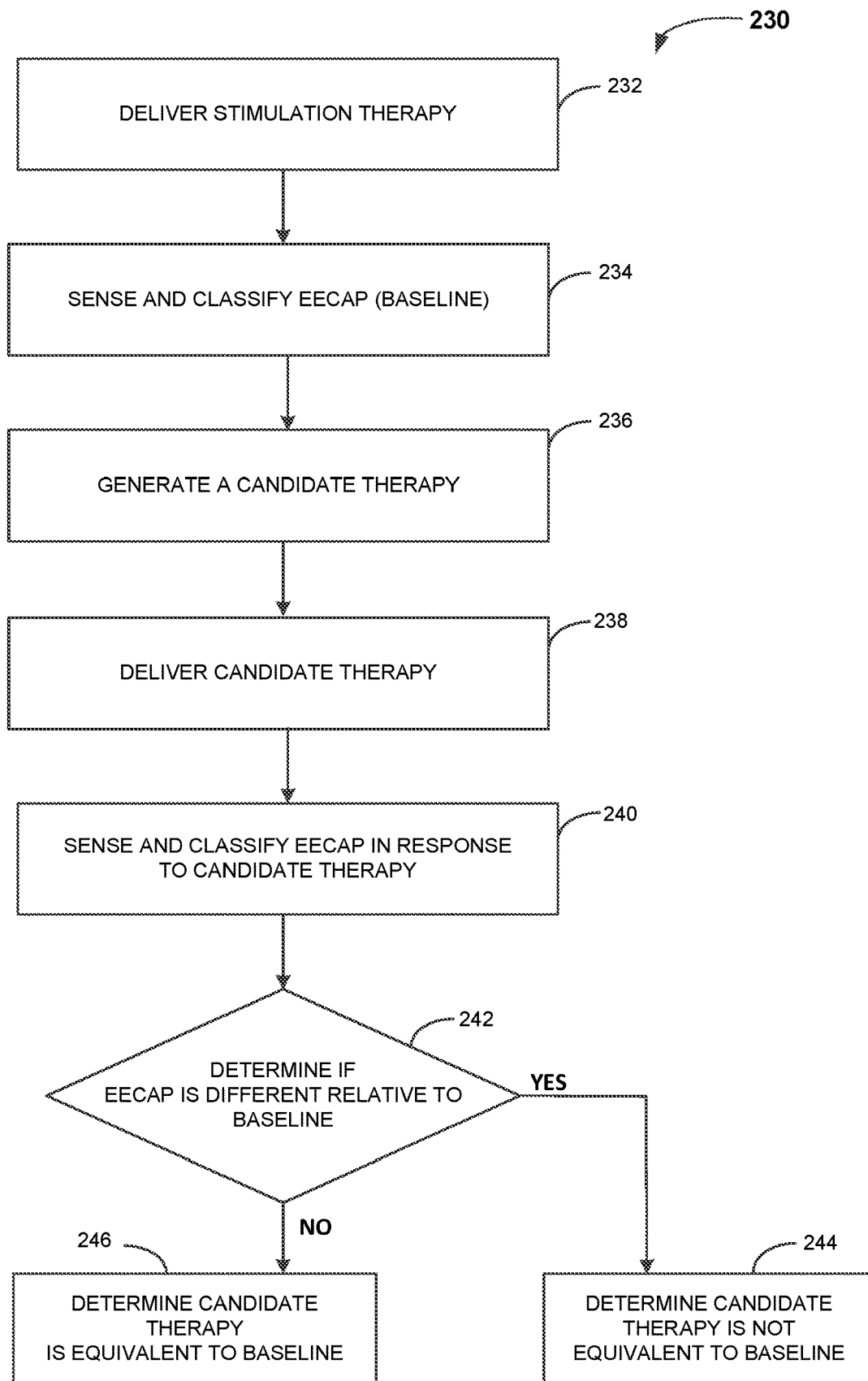
FIG. 10 is a flow diagram illustrating an example method for testing electrical stimulation therapy parameters based on a sensed eECAP in response to applied stimulation in accordance with various techniques consistent with this disclosure.

FIG. 10 is a flow diagram illustrating an example method 230 for testing electrical stimulation therapy parameters based on a sensed eECAP in response to applied stimulation in accordance with various techniques consistent with this disclosure. Although discussed with respect to IMD 14 of FIG. 1, the method 230 of FIG. 10 may be implemented, in whole or in part, by system 22 of FIG. 2, and may be implemented, in whole or in part, by system 120 of FIG. 5. In various examples, method 230 may be performed in whole or in part by any of the processing circuitry described herein. In various examples, it may be desirable to test a proposed stimulation therapy that comprise one or more therapy parameters that are unlike any set of therapy parameters that have been applied as stimulation therapy to a patient, but that might provide some feature or advantage, such as better patient comfort or safety, or better system performance, such as longer battery life, but that may only be useful if the proposed therapy parameters provide an equivalent level of treatment efficacy, or at least some minimum level of treatment efficacy. The use of the eECAP according the method 230 provides a method to evaluate these proposed treatments as follows.

As illustrated in method 230, IMD 14 delivers electrical stimulation as a therapeutic or a diagnostic intervention (stimulation therapy) to a patient (block 232). IMD 14 senses an eECAP signal generated by one or more nerve fiber bundles in response to the delivered electrical stimulation, and classifies the sensed eECAP signal as a baseline signal (block 234). Method 200 further includes generation of a candidate therapy (block 236). In some examples, the therapy parameters for the candidate therapy may be provided as an input from a clinician or a physician, such as by using programmer 20, to allow inputs regarding the desired therapy parameters for the candidate therapy, and to communicate these parameters to IMD 14 in any of the techniques described herein. In various examples, the parameters for the candidate therapy may be parameters that were previously stored n IMD 14. In various examples, the parameters for candidate therapy may include some parameters provided to IMD 14, for example from programmer 20, and other parameters that were previously stored in IMD 14. In various examples, one or more of the therapy parameters for the candidate therapy may be automatically generated by IMD 14. In some examples, generation of the candidate therapy parameters may be determined based at least in part on a detected change in activity level or a detected posture of the patient.

Once the candidate therapy based on the candidate therapy parameters has been defined and generated, IMD 14 delivers the candidate therapy to a patient (block 238). Following delivery of the candidate therapy, IMD 14 senses an eECAP signal generated by the one or more nerve fiber bundles in response to the delivered candidate therapy, and classifies the sensed eECAP signal (block 240). Classification of the sensed eECAP signal may comprise measurement and/or derivation of any type of parameter associated with the sensed eECAP signal, and comparison of these parameters to the corresponding parameters associated with the eECAP baseline.

Based on the sensed and classified eECAP signal, IMD 14 determines if the sensed and classified eECAP signal is different from the baseline (block 242). If IMD 14 determines that the sensed and classified eECAP signal is not different from the baseline (a "NO" output from block 242), then a determination has been made that the candidate therapy is equivalent to the baseline therapy (block 246). In the alternative, if IMD 14 determines that the sensed and classified eECAP signal is different from the baseline (a "YES" output from block 242), then a determination has been made that the candidate therapy is not equivalent to the baseline therapy (block 246). By determining that the candidate therapy is equivalent to the baseline, the candidate therapy may be provided to a patient to achieve the same level of efficacy of treatment that is provided by the therapy treatment used to generate the baseline, but with the advantages provided by using the parameters of the candidate therapy. On the other hand, if the candidate therapy is determined to not be equivalent to the baseline, then the candidate therapy is also determined to not necessarily be capable of providing a same level of efficacy of treatment provided by the therapy treatment used to generate the baseline.

In various examples, the difference between the eECAP signal generated in response to the candidate therapy and the eECAP signal generated in response to the therapy treatment that generated the baseline may be used to evaluate tradeoffs between the two therapy treatments. For example, if the difference allows for a saving of some percentage of battery power using the candidate therapy, but the time between applications of the candidate therapy is decreased (e.g., therapy needs to be applied more often), a conscious decision could be made to use the candidate therapy in order to increase battery life at the expense of more frequent application of therapy. Many other types of comparisons and trade-off analysis would be possible by comparison of the eECAP response generated by the candidate therapy to the baseline, and are contemplated by use of method 230.

Figure 11:
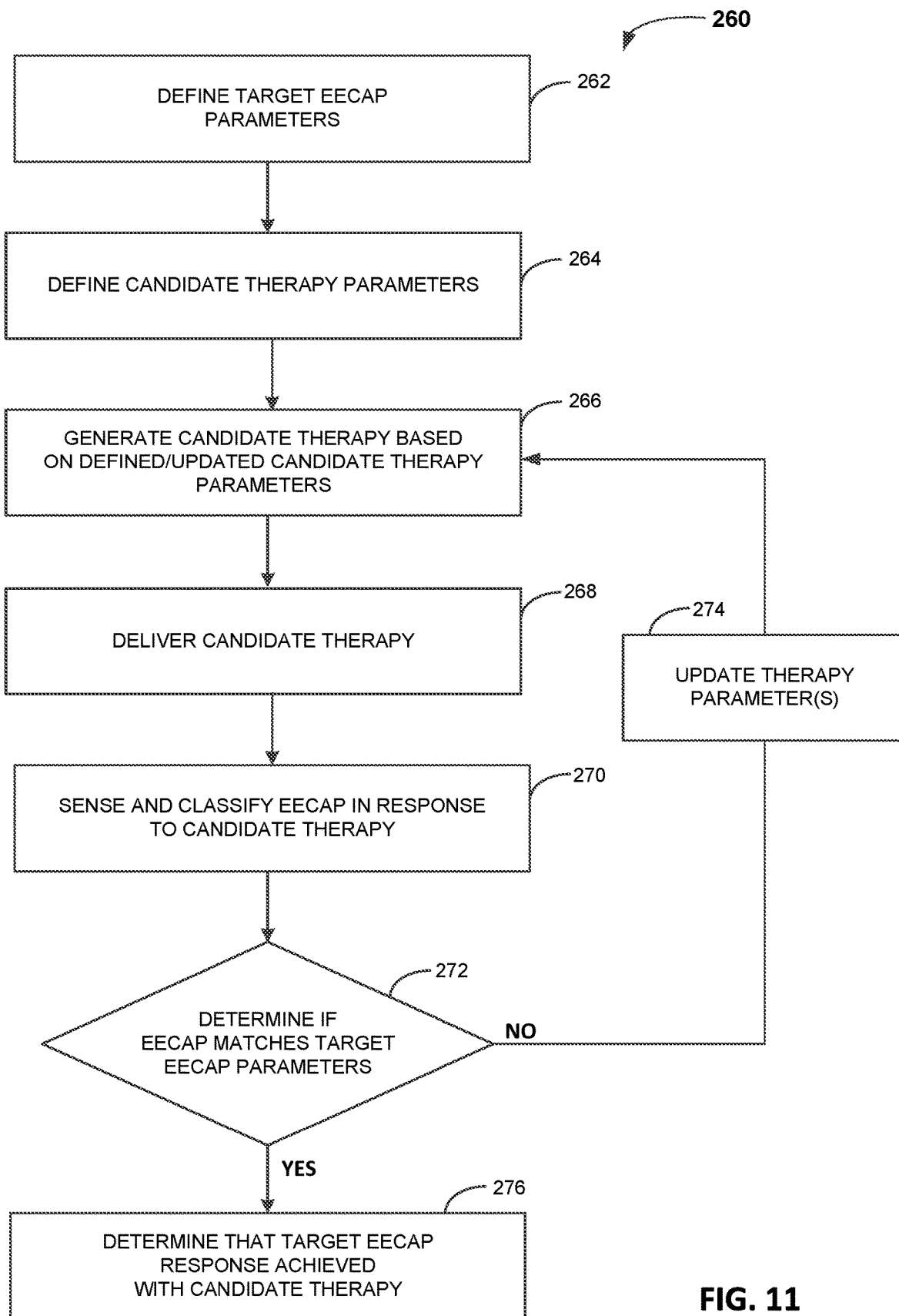
FIG. 11 is a flow diagram illustrating an example method for adjusting electrical stimulation therapy parameters based on a sensed eECAP in response to applied stimulation in accordance with various techniques consistent with this disclosure.

FIG. 11 is a flow diagram illustrating an example method 260 for adjusting electrical stimulation therapy parameters based on a sensed eECAP in response to applied stimulation in accordance with various techniques consistent with this disclosure. Although discussed with respect to IMD 14 of FIG. 1, the method 260 of FIG. 11 may be implemented, in whole or in part, by system 22 of FIG. 2, and may be implemented, in whole or in part, by system 120 of FIG. 5. In various examples, method 260 may be performed in whole or in part by any of the processing circuitry described herein. In various examples, it is desirable to adapt therapy to a particular set of eECAP parameters that are known to provide a therapeutically optimal state. As an example, an eECAP initial area under the curve of 20 µV/millisecond with a τ (time) of 15 seconds may be optimal for a particular patient. The therapy pulse shape, amplitude, and/or frequency may be varied in one or more combinations, and delivered as candidate therapies until a candidate therapy that provides the particular set of eECAP parameters in an eECAP signal generated in response to application of the candidate therapy to the patient is achieved.

As shown for method 260, a set of target eECAP parameters is defined (block 262). In various examples the target eECAP parameters are parameters that are known to provide a particular therapeutically state, for example a therapeutic state that is optimal for a patient. A set of candidate therapy parameters is defined (block 264). In various examples, the candidate therapy parameters are a set of parameters that initially are not known to provide the therapy efficacy and or performance levels for a system when provided by a therapy device, such a s IMD 14, to a patient. In various examples, the candidate therapy parameters are determined based on one or more constraints for delivering stimulation therapy to the patient, such as a maximum level of a parameter that may be provided in association with a stimulation therapy, or for example by a system constraint providing a limit to a parameter that can be provided by the system used to apply the stimulation therapy to the patient. For example, a maximum voltage level that a therapy system can deliver, or that may be safely delivered to a patient, may be a constraint on the candidate therapy parameters. In another example, a maximum frequency of the delivered stimulation therapy than can be generated by the device generating and/or delivering the therapy, may be a constraint on the therapy parameters that are possible for us in the candidate therapy. In some examples, defining the candidate therapy parameters may be determined based at least in part on a detected change in activity level or a detected posture of the patient.

Once the candidate therapy parameters are defined, IMD 14 generates the candidate therapy based on the defined candidate therapy parameters (block 266). IMD 268 then delivers the candidate therapy (block 268). IMD 14 senses and classifies the eECAP signal generated in response to the application of the candidate therapy to the patient (block 270). Classification of the sensed eECAP signal may comprise measurement and/or derivation of any type of parameter associated with the sensed eECAP signal, and comparison of these measurements to a baseline. IMD 14 then determines if the sensed and classified eECAP signal matches the target eECAP parameters (block 272). A determination of whether the sensed and classified eECAP signal "matches" the target eECAP signal is not limited to a determination based on any particular criteria, and may be based on comparison of one or more parameters associated with the sensed and classified eECAP signal to the corresponding parameters associated with the target eECAP signal. If IMD 14 determines that the sensed and categorized eECAP signal does not match the target eECAP parameters (a "NO" output from block 272), then a determination has been made that the candidate therapy is not equivalent to the baseline therapy, and in some examples of method 260, the candidate therapy parameters are updated (block 274). Updating the candidate therapy parameters at block 274 may be performed automatically, for example by IMD 14, or may be performed by virtue of new inputs received for example from programmer 20 to IMD 14, the inputs provided in some examples by a clinician or a physician. In some examples, updating of the candidate therapy parameters may be determined based at least in part on a detected change in activity level or a detected posture of the patient.

The further updated therapy parameter is then provided to block 266, wherein IMD 14 uses the updated therapy parameter to generate a new candidate therapy using the updated parameter. The candidate therapy generated using the updated parameter is delivered to the patient (block 268). IMD 14 again senses the eECAP signal generated by the one or more nerve fiber bundles in response to the delivered candidate therapy, and again classifies the sensed eECAP signal (block 270). Again, IMD 14 determines if the sensed eECAP signal generated in response to the candidate therapy including the most recently updated parameter matches the target eECAP parameters (block 272). If IMD 14 again determines that the sensed eECAP signal generated in response to the candidate therapy does not match the target eECAP parameters, a "NO" output is generated (at block 272), and the process of method 200 moves again back to block 274 to update the therapy parameters. In various examples of method 260, the number of times the therapy parameter is updated and a new candidate therapy is generated and delivered based on the updated therapy parameter is not limited to any particular number of iterations. In some examples, the process of updating therapy parameters, generating and delivering candidate therapy based the updates to the therapy parameter, sensing and classifying the eECAP signal that occurred in response to the candidate therapy, and determining if the eECAP signal matches the target eECAP parameters can be performed until a "YES" output is generated at block 272.

If at block 272 IMD 14 determines that that the sensed and categorized eECAP signal does match the target eECAP parameters (a "YES" output from block 272), then a determination is made the target eECAP signal response has been achieved by the application of the candidate therapy to the patient. This determination may indicate that the candidate therapy may be provided to the patient to produce the targeted eECAP response, and thus the desired therapy efficacy and/or a desired set of performance parameters for the system delivering the stimulation to the patient.

Figure 12:
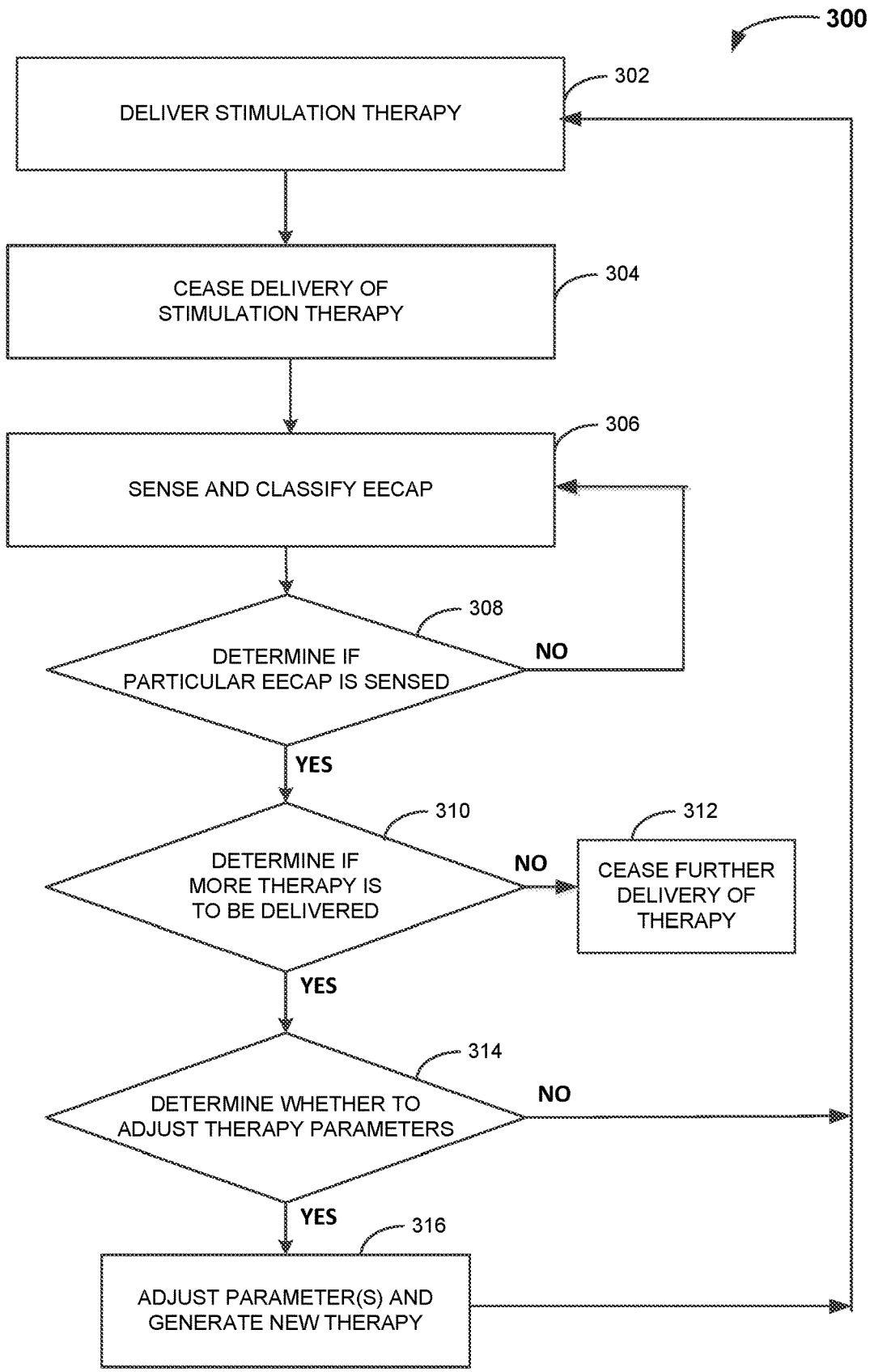
FIG. 12 is a flow diagram illustrating an example method for adjusting electrical stimulation therapy parameters based on a sensed eECAP in response to applied stimulation in accordance with various techniques consistent with this disclosure.

FIG. 12 is a flow diagram illustrating an example method 300 for adjusting electrical stimulation therapy parameters based on a sensed eECAP in response to applied stimulation in accordance with various techniques consistent with this disclosure. Although discussed with respect to IMD 14 of FIG. 1, the method 300 of FIG. 12 may be implemented, in whole or in part, by system 22 of FIG. 2, and may be implemented, in whole or in part, by system 120 of FIG. 5. In various examples, method 300 may be performed in whole or in part by any of the processing circuitry described herein. In various examples, characteristics of the eECAP may be used to trigger delivery of a pre-defined neurostimulation therapy. For instance, a particular electrical stimulation therapy can be delivered to the dorsal column or the neural target. Following cessation of the therapy, eECAP can be used as a tool to monitor the dynamics of the neural target previously stimulated until a particular eECAP is seen. The occurrence of this particular eECAP can be used as a trigger to deliver more therapy. In other examples, the occurrence of this particular eECAP can be used as a trigger to cease deliver of further therapy.

As illustrated in method 300, IMD 14 delivers electrical stimulation therapy to a patient (block 302). At some point in time, IMD ceases delivery of the stimulation therapy (block 304). IMD 14 then senses an eECAP signal generated by one or more nerve fiber bundles in response to the delivered electrical stimulation, and classifies the sensed eECAP signal. Classification of the sensed eECAP signal is not limited to any particular means of classification, and in some examples comprises determining one or more parameters directly measured from and/or derived from the parameters of sensed eECAP signal. Classification of the eECAP signal in various examples incudes determining whether the parameters associated with the sensed eECAP signal include values that fall with a given range of values for the parameter, or in some examples if the value of one or more parameters associated with the sensed eECAP signal exceeds a predetermined threshold value, or does not exceed a predetermined threshold value.

At block 308, IMD 14 determines if a particular eECAP is sensed (block 308). In some examples, determining if a particular eECAP is sensed comprises comparing a value for one or more of the parameters associated with the sensed eECAP signal to a template and/or to one or more predetermined values for the one or more parameters. If a determination is made that the sensed eECAP is not the particular eECAP (a "NO" is generated at block 308), then method returns to block 306, and again senses and classifies the eECAP signal at this later time. In the alternative, if a determination is made at block 308 that the particular eECAP is sensed (a "YES" is generated at block 308), and method 300 proceeds to block 310.

At block 310, IMD 14 determines if more therapy is to be delivered. In some examples, determining if more therapy is to be delivered is based on a predetermined rule programmed or otherwise stored in IMD 14 that dictates whether more therapy is to be delivered when the particular eECAP is sensed. In some examples, a determination of whether more therapy is to be delivered may be based at least in part on a detected change in activity level or a detected posture of the patient. If a determination is made at block 310 that no more therapy is to be delivered, (a "NO" is generated at block 310), then method proceeds to block 312, were IMD 14 ceases further delivery of stimulation therapy. In the alternative, if a determination is made at block 310 that more therapy is to be delivered, (a "YES" is generated at block 310), and method 300 proceed to block 314.

At block 314, IMD 14 determines whether to adjust therapy parameters. In some examples, determining whether to adjust therapy parameters is based on a predetermined rule programmed or otherwise stored in IMD 14. For example, IMD 14 may be running a pre-programmed set of stimulation therapies as part of method 300 that sets up incremental changes for one or more of the therapy parameters used to deliver therapy at block 302. In some examples, a determination of whether to adjust the therapy parameters may be based at least in part on a detected change in activity level or a detected posture of the patient.

As such, IMD 14 at block 314 may determine that an adjustment of one or more of the therapy parameters is required, and generates a "YES" output at block 314. If IMD 14 generates a "YES" output at block 314, method 315 proceeds to block 316. At block 316, IMD 14 adjusts one or more therapy parameters, and generates a new therapy based on the updated therapy parameters. Once the new therapy has been generated, method 300 proceeds to block 302, wherein at block 302 IMD 14 delivers stimulation therapy based on the new therapy and the adjusted therapy parameters, and IMD 14 continues to execute the processes of method 300 as described above. The number of iteration of adjusting therapy parameters and delivering stimulation therapy based on the new therapy is not limited to any particular number iterations, and in some examples continues until IMD 14 determines that no more therapy is to be delivered at block 310.

In the alternative, if at block 314 IMD 14 determination that no adjustments to the therapy parameters are to be made, (a "NO" output is generated at block 314), and method 300 proceeds to block 302, wherein IMD 14 delivers stimulation therapy based on the therapy parameters used in conjunction with the mort recently applied stimulation therapy. After delivering stimulation therapy at block 302, IMD 14 continues to execute the processes of method 300 as described above.

Figure 13:
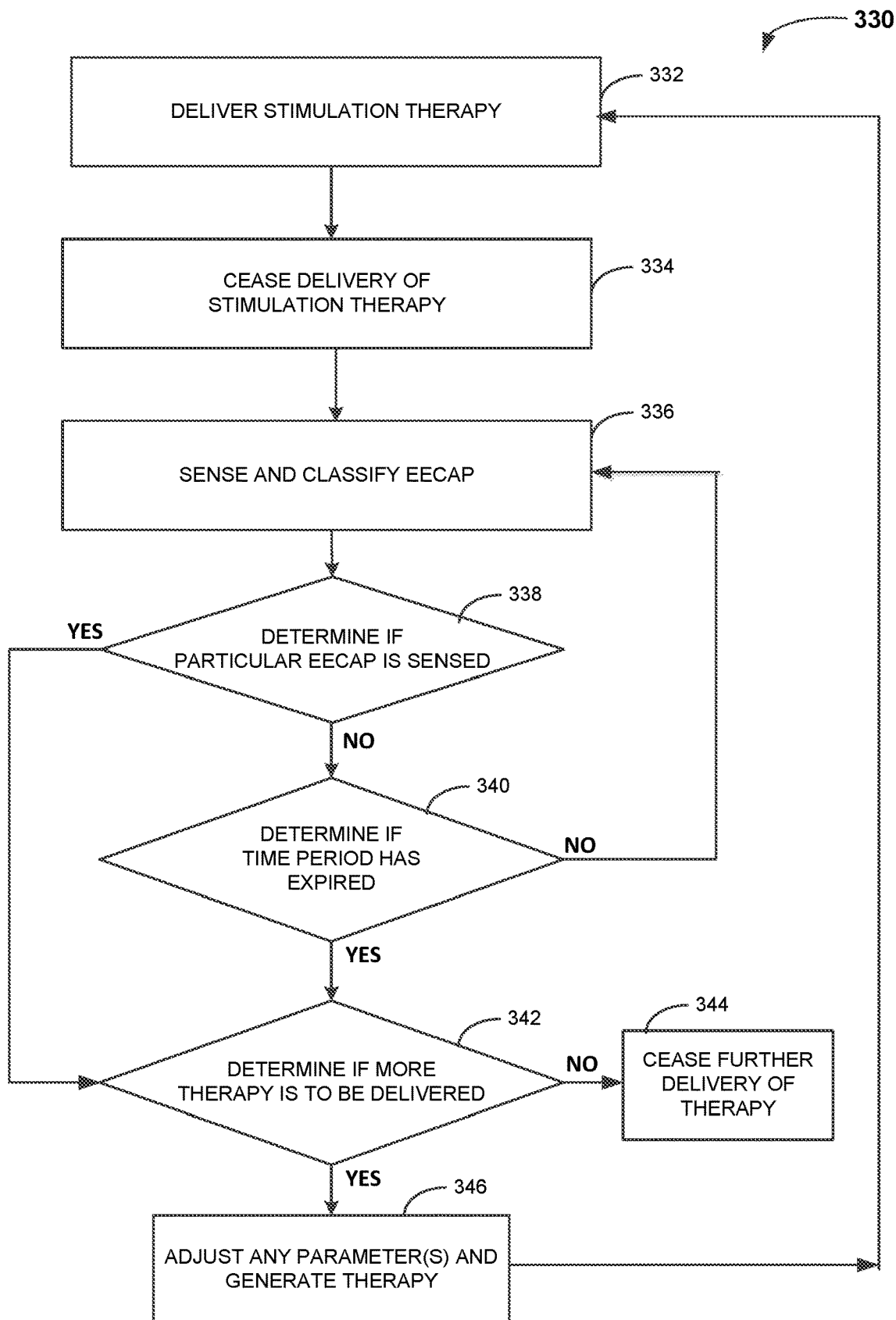
FIG. 13 a flow diagram illustrating an example method for adjusting electrical stimulation therapy parameters based on a sensed eECAP in response to applied stimulation in accordance with various techniques consistent with this disclosure.

FIG. 13 a flow diagram illustrating an example method 330 for adjusting electrical stimulation therapy parameters based on a sensed eECAP in response to applied stimulation in accordance with various techniques consistent with this disclosure. Although discussed with respect to IMD 14 of FIG. 1, the method 330 of FIG. 13 may be implemented, in whole or in part, by system 22 of FIG. 2, and may be implemented, in whole or in part, by system 120 of FIG. 5. In various examples, method 330 may be performed in whole or in part by any of the processing circuitry described herein. In various examples, time may also be used as part of a feedback loop. For instance, a neurostimulation therapy may be delivered to the neural target. The system may decide to deliver or not deliver further neurostimulation therapy based on a determination as to whether a specific eECAP is or isn't seen within a fixed period of time relative to the delivery of the neurostimulation therapy.

As illustrated, in method 330 IMD 14 delivers electrical stimulation therapy to a patient (block 332). At some point in time, IMD ceases delivery of the stimulation therapy (block 334). IMD 14 then senses an eECAP signal generated by one or more nerve fiber bundles in response to the delivered electrical stimulation, and classifies the sensed eECAP signal (block 336). Classification of the sensed eECAP signal is not limited to any particular means of classification, and in some examples comprises determining one or more parameters directly measured from and/or derived from the parameters of sensed eECAP signal. Classification of the eECAP signal in various examples incudes determining whether the parameters associated with the sensed eECAP signal include values that fall with a given range of values for the parameter, or in some examples if the value of one or more parameters associated with the sensed eECAP signal exceed or do not exceed a predetermined threshold value set for the corresponding parameter.

Following sensing and classification of the eECAP signal, IMD 14 determines if a particular eECAP is sensed (block 338). In some examples, determining if a particular eECAP is sensed comprises comparing a value for one or more of the parameters associated with the sensed eECAP signal to a template and/or to one or more baseline values for the one or more parameters. If a determination is made that the sensed eECAP is not the particular eECAP (a "NO" is generated at block 338), then method 330 proceeds to block 340, and wherein IMD 14 determines if a predetermined time limit for either sensing or for not sensing the particular eECAP signal has expired. If the predetermined time limit has not expired (a "NO" is generated at block 340), method 330 returns to block 336, wherein IMD 14 again senses and classifies the eECAP signal. In the alternative, if the predetermine time limit has expired (a "YES" is generated at block 340), method 330 proceeds to block 342, where IMD 14 determines if more therapy is to be delivered. In some examples, a determination of whether more therapy is to be delivered may be based at least in part on a detected change in activity level or a detected posture of the patient. If IMD 14 determines that no more therapy is to be delivered (a "NO" is generated at block 342), method 330 proceed to block 344, wherein IMD 14 ceased to further delivery of stimulation therapy. If in the alternative IMD 14 determines at block 342 that more therapy is to be delivered (a "YES" is generated at block 342), method 330 proceed to block 346.

At block 346, IMD 14 may adjust any parameters to the therapy parameters that will be utilized during next stimulation therapy to be applied to the patient, generates the next stimulation therapy, and method 330 then returns to block 332, where IMD 14 delivers the new stimulation therapy. In some examples, the new stimulation therapy is delivered using the same set of therapy parameters used in the generation and delivery of the previously delivered stimulation therapy. In some examples, the new stimulation therapy is delivered using one or more therapy parameters that are different in value from the therapy parameters used in the previously delivered stimulation therapy. In some examples, a determination of whether to adjust any therapy parameters may be based at least in part on a detected change in activity level or a detected posture of the patient.

Referring back to block 338, if after sensing and classifying the eECAP signal IMD 14 determines that the particular eECAP signal was sensed, method 330 proceeds to block 342, where a determination as to whether more therapy is to be delivered is made, as described above. Once at block 342, method 330 proceeds as described above, wherein IMD 14 may either cease further delivery of stimulation therapy, or may adjust one or more parameters and generate a new stimulation therapy for delivery to the patient. Determinations as to whether more therapy is to be delivered based on sensing or not sensing a particular eECAP signal are not limited to any particular decision criteria, and may be based on rules defined by a clinician and/or a physician and stored in IMD 14 for use in the decisions made as part of the processes performed by method 330.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples of the devices, systems, and methods in accordance with the description provided in this disclosure are provided below.

Example 1

A method comprising: delivering, by a stimulation electrode, electrical stimulation as a candidate therapy to a patient according to a set of candidate therapy parameters, the stimulation electrode located in proximity to the dorsal column of a patient; sensing, by a sensing electrode, an electrically evoked compound action potential (eECAP) signal in response to the delivery of the electrical stimulation; classifying, by a processor, the sensed eECAP signal generated in response to the application of the candidate therapy relative to an eECAP baseline; and determining, by the processor, if the sensed eECAP signal is different over the eECAP baseline based on at least one parameter used in classifying the sensed eECAP signal.

Example 2

The method of example 1, wherein classifying the sensed eECAP signal comprises classifying the sensed eECAP signal based on the at least one parameter directly measured from or derived from the at least one parameter of the sensed eECAP signal.

Example 3

The method of example 2, wherein classifying the sensed eECAP signal based on the at least one parameter comprises comparing a value for the parameter to a value or a range of values for a corresponding parameter measured or derived from a baseline eECAP signal used to generate the eECAP baseline.

Example 4

The method of any one of examples 2-3, wherein the parameter measured or derived from the sensed eECAP signal comprises a measure of fiber latency in the sensed eECAP signal.

Example 5

The method of any of examples 2-4, wherein the parameter measured or derived from the sensed eECAP signal comprises a measure of a time when masking occurs for a portion of the sensed eECAP signal attributed to a specific nerve fiber type.

Example 6

The method of any of examples 2-5, wherein the parameter measured or derived from the sensed eECAP signal comprises a measurement of the width of the eECAP signal.

Example 7

The method of any of examples 2-6, wherein the parameter measured or derived from the eECAP signal comprises an amplitude of the eECAP signal.

Example 8

The method of any of examples 2-7, wherein the parameter measured or derived from the eECAP signal comprises an area under a portion of a curve of the amplitude of the eECAP signal.

Example 9

The method of any of examples 2-8, wherein the parameter measured or derived from the eECAP signal comprises a ratio of eECAP amplitude for the eECAP signal attributed to a first nerve fiber type versus the eECAP amplitude for the eECAP signal attributed to a second nerve fiber type differ from the first nerve fiber type.

Example 10

The method of any of examples 2-9, wherein parameter measured or derived from the eECAP signal comprises a difference value between the fiber latency for a first nerve fiber type with respect the fiber latency for a second nerve fiber type that is a different nerve fiber type than the first nerve fiber type.

Example 11

The method of any of examples 2-10, wherein classifying the sensed eECAP signal based on the parameter measured or derived from the sensed eECAP signal comprises determining if a value of the parameter from the sensed eECAP signal does not exceed a threshold value determined for the corresponding parameter value of the eECAP baseline.

Example 12

The method of any of examples 2-11, wherein classifying the sensed eECAP signal based on the parameter measured or derived from the sensed eECAP signal comprises determining if a value of the parameter from the sensed eECAP falls within a predetermined range of values determined by a corresponding parameter value of the eECAP baseline.

Example 13

The method of any of examples 1-12, further comprising: determining, by the processor, whether to adjust one or more of the therapy parameters used to deliver stimulation therapy to a patient based on the classification of the sensed eECAP signal.

Example 14

The method of any of examples 1-13, where classifying the sensed eECAP signal relative to the eECAP baseline comprises determining whether the sensed eECAP signal is equivalent to the eECAP baseline.

Example 15

The method of any of examples 1-14, wherein the eECAP baseline is established by applying a baseline stimulation therapy having a set of baseline set of therapy parameters to a patient, and sensing an eECAP signal generated as a result of the application of the baseline stimulation therapy.

Example 16

The method of any of examples 1-15, further comprising: detecting a change in patient posture from a first posture state to a second posture state; and in response to detection of the change in patient posture, detecting a second signal including the eECAP in response to the application of the stimulation therapy.

Example 17

The method of example 16, further comprising: responsive to detecting the change in patient posture, applying the stimulation therapy according to a second set of stimulation therapy parameters associated with the second posture state; detecting the second signal including the eECAP in response to the application of stimulation therapy according to the second set of stimulation therapy parameters; and adjusting one or more of the stimulation parameters of the second set of stimulation parameters based on the detected signal.

Example 18

The method of any of examples 1-17, wherein the eECAP baseline is a stored eECAP signal.

Example 19

The method of any of examples 1-18, further comprising detecting the signal including the eECAP in response to the application of the stimulation therapy at a predetermined time interval following cessation of the application of the stimulation therapy.

Example 20

The method of any of claims 1-19, wherein electrical stimulation as a candidate therapy comprises at least one therapy parameter having a value that is different from the value of the corresponding therapy parameter applied as electrical stimulation to the patient in order to generate the eECAP baseline.

Example 21

The method of example 20, wherein the at least one therapy parameter of the of the candidate therapy that is different from the value of the corresponding therapy parameter applied as electrical stimulation to the patient in order to generate the eECAP baseline, comprises candidate therapy having a higher frequency.

Example 22

The method of example 21, wherein the higher frequency comprises a frequency in a range of 10-15 kHz.

Example 23

The method of any of examples 1-22, wherein determining, by the processor, if the sensed eECAP signal is different over the eECAP baseline based on at least one parameter used in classifying the sensed eECAP signal further comprises: determining, by the processor, that the sensed eECAP signal is different over the eECAP baseline; and establishing, by the processor, a parameter boundary for at least one of the therapy parameters used to generate a candidate therapy that was applied to the patient and resulted in a sensed and categorized eECAP signal that was not different from the baseline.

Example 24

The method of any of examples 1-23, wherein determining, by the processor, if the sensed eECAP signal is different over the eECAP baseline based on at least one parameter used in classifying the sensed eECAP signal further comprises: determining, by the processor, that the sensed eECAP signal is not different over the eECAP baseline; updating, by the processor at least one therapy parameter of the candidate therapy and generating a new candidate therapy based on the updated therapy parameter; delivering, by a stimulation electrode, electrical stimulation as a new candidate therapy to a patient according the new candidate therapy parameters, sensing, by a sensing electrode, an electrically evoked compound action potential (eECAP) signal in response to the delivery of the electrical stimulation; classifying, by a processor, the sensed eECAP signal generated in response to the application of the new candidate therapy relative to an eECAP baseline; and determining, by the processor, if the sensed eECAP signal is different over the eECAP baseline based on at least one parameter used in classifying the sensed eECAP signal.

Example 25

A system comprising: one or more electrodes; a stimulation generator configured to apply stimulation therapy via the one or more electrodes based on a set of stimulation therapy parameters; and a processor configured to: generate the candidate therapy parameters, control the stimulation generator to provide the candidate stimulation therapy to the one or more electrodes based on the candidate therapy parameters, sense an electrically evoked compound action potential (eECAP) signal generated in response to the application of the candidate stimulation therapy, classify the sensed eECAP signal based on an eECAP baseline; and determine if the sensed eECAP signal is different over the eECAP baseline based on at least one parameter used in classifying the sensed eECAP signal.

Example 26

The system of example 25, further comprising a memory configured to store stimulation parameters, wherein the processor is configured to generate a third set of stimulation parameters including the one or more stimulation parameters in association with a change in posture state of the patient, and store the third set of stimulation parameters in the memory.

Example 27

The system of any of examples 25-26, wherein the processor is further configured to: compare one or more parameters of the sensed eECAP to one or more corresponding parameters of the eECAP baseline; and adjust at least one of the stimulation parameters based on the comparison; wherein the one or more electrodes are further configured to provide stimulation therapy based on an adjusted set of stimulation therapy parameters.

Example 28

The system of any of examples 25-27, wherein the processor is further configured to detect a signal including an eECAP in response to the application of the stimulation therapy at a predetermined interval from the application of the stimulation therapy.

Example 29

The system of any of examples 25-28, further comprising a memory configure to store the set of stimulation parameters including at least one adjusted stimulation parameter.

Example 30

The system of any of examples 25-29, wherein the one or more electrodes are further configured to detect a signal including the eECAP by electrodes located at a distance from the targeted stimulation nerve site.

Example 31

The system of any of examples 25-30, wherein the one or more electrodes are further configured to apply the stimulation therapy to a dorsal column of a patient.

Example 32

A system comprising: one or more electrodes; a stimulation generator configured to apply stimulation therapy via the one or more electrodes based on a set of stimulation therapy parameters; and a processor configured to: receive a detected signal including an evoked compound action potential (eECAP) in response to the application of the stimulation therapy; analyze the detected signal; and adjust at least one of the stimulation parameters based on the analysis of the detected signal.

Example 33

The system of example 32, further comprising: a posture state module configured to detect a posture state of a patient; andwherein the processor is further configured to detect a change in the posture state from a first posture state to a second posture state, and in response to detection of the change in patient posture from the first posture state to the second posture state, detect the signal including an eECAP in response to the application of the stimulation therapy.

Example 34

The system of example 33, further comprising: wherein the set of stimulation parameter comprises a first set of stimulation parameters; wherein the stimulation generator is further configured to provide stimulation according to a second set of stimulation therapy parameters associated with the second posture state; and wherein the processor is further configured to: detect the signal including an eECAP in response to the application of stimulation therapy according to the second set of stimulation therapy parameters; and adjust at least one of the stimulation parameters of the second set of stimulation parameters based on the eECAP detected in response to application of the second set of stimulation therapy parameters.

Example 35

A system comprising: means for applying stimulation therapy to a patient according to a set of stimulation therapy parameters; means for sensing a signal including an electrically evoked compound action potential (eECAP) in response to the application of the stimulation therapy; and means for classifying the sensed eECAP signal at least in part based on a baseline eECAP.

Example 36

The system of example 35, wherein the means for classifying the sensed eECAP signal comprises means for classifying the sensed eECAP signal based on a parameter measured or derived from the sensed eECAP signal.

Example 37

The system of any of examples 35-36, further comprising means for performing any of the methods descried herein.

Example 38

A non-transitory computer readable medium comprising instructions for causing a programmable processor to perform any of the methods described in examples 1-24.

Example 39

A non-transitory computer readable medium comprising instructions for causing a programmable processor to perform any of the methods described herein.

Example 40

A method comprising: delivering, by a stimulation electrode, electrical stimulation as a baseline therapy to a patient according to a set of baseline therapy parameters, the stimulation electrode located in proximity to the dorsal column of the patient; sensing, by a sensing electrode, an electrically evoked compound action potential (eECAP) signal in response to the delivery of the electrical stimulation as an eECAP baseline; determining, by a processor, a change to a therapy parameter to generate a candidate therapy having a set of candidate therapy parameters; delivering, by the stimulation electrode, electrical stimulation based on the candidate therapy to the patient according to the candidate therapy parameters; sensing, by the sensing electrode, an electrically evoked compound action potential (eECAP) signal in response to the delivery of the electrical stimulation based on the candidate therapy; classifying, by the processor, the sensed eECAP signal generated in response to the application of the candidate therapy relative to an eECAP baseline; determining, by the processor, if the sensed eECAP signal is different over the eECAP baseline based on at least one parameter used in classifying the sensed eECAP signal; and establishing, by the processor, a parameter boundary for the at least one parameter as equivalent to the baseline if the sensed eECAP signal is determined to be different over the eECAP baseline.

Example 41

A method comprising: delivering, by a stimulation electrode, electrical stimulation as a baseline therapy to a patient according to a set of baseline therapy parameters, the stimulation electrode located in proximity to the dorsal column of the patient; sensing, by a sensing electrode, an electrically evoked compound action potential (eECAP) signal in response to the delivery of the electrical stimulation as an eECAP baseline; generating, by a processor, a candidate therapy having a set of candidate therapy parameters; delivering, by the stimulation electrode, electrical stimulation as a candidate therapy to the patient accord to the set of candidate therapy parameters; sensing, by the sensing electrode, an electrically evoked compound action potential (eECAP) signal in response to the delivery of the electrical stimulation based on the candidate therapy; classifying, by the processor, the sensed eECAP signal generated in response to the application of the candidate therapy relative to an eECAP baseline; and determining, by the processor, if the sensed eECAP signal is different over the eECAP baseline based on at least one parameter used in classifying the sensed eECAP signal, wherein determining if the sensed eECAP signal is different over the eECAP baseline comprises deterring that the candidate therapy is equivalent to the baseline therapy if the sensed eECAP signal is not different over the eECAP baseline, or that the candidate therapy is not equivalent to the baseline therapy if the sensed eECAP signal is different over the eECAP baseline.

Example 42

A method comprising: defining, by a processor, one or more target parameters for an electrically evoked compound action potential (eECAP) signal as a target eECAP; defining, by the processor, one or more candidate therapy parameters; generating, by the processor, a candidate therapy based on as set of the defined candidate therapy parameters; delivering, by a stimulation electrode, electrical stimulation based on the generated candidate therapy to a patient according to the set of candidate therapy parameters, the stimulation electrode located in proximity to the dorsal column of the patient; sensing, by a sensing electrode, an electrically evoked compound action potential (eECAP) signal in response to the delivery of the candidate therapy; classifying, by the processor, the sensed eECAP signal generated in response to the application of the candidate therapy relative to the target eECAP; and determining, by the processor, if the sensed eECAP signal matches the target eECAP based on at least one parameter used in classifying the sensed eECAP signal, wherein determining if the sensed eECAP signal matches the target eECAP comprises deterring that the at least one parameter used in classifying the sensed eECAP signal matches the corresponding parameter or parameters of the target eECAP.

Example 43

A method comprising: delivering, by a stimulation electrode, electrical stimulation as a baseline therapy to a patient according to a set of baseline therapy parameters, the stimulation electrode located in proximity to the dorsal column of the patient; ceasing delivery of the electrical stimulation by the stimulation electrode; sensing, by a sensing electrode, an electrically evoked compound action potential (eECAP) signal in response to the delivery of the electrical stimulation as an eECAP signal; classifying, by a processor, the sensed eECAP signal generated in response to the application of the baseline therapy relative to an eECAP baseline; determining, by the processor, if the sensed eECAP is a particular eECAP, the determination of whether the sensed eECAP is a particular eECAP based on one or more parameters used to classify the sensed eECAP signal; and determining, by the processor, if more therapy is to be delivered to the patient based on the determination of whether the sensed eECAP was or was not the particular eECAP.

Example 44

A method comprising: delivering, by a stimulation electrode, electrical stimulation as a baseline therapy to a patient according to a set of baseline therapy parameters, the stimulation electrode located in proximity to the dorsal column of the patient; ceasing delivery of the electrical stimulation by the stimulation electrode; sensing, by a sensing electrode, an electrically evoked compound action potential (eECAP) signal in response to the delivery of the electrical stimulation as an eECAP signal; classifying, by a processor, the sensed eECAP signal generated in response to the application of the baseline therapy; determining, by the processor, if the sensed eECAP is a particular eECAP, the determination of whether the sensed eECAP is a particular eECAP based on one or more parameters used to classify the sensed eECAP signal; determining, by the processor, if a time period has expired following ceasing delivery of the electrical stimulation; and determining, by the processor, if more therapy is to be delivered to the patient based on the determination of whether the sensed eECAP was or was not the particular eECAP and whether the time period has expired.

Various examples consistent with this disclosure have been described. These and other examples are within the scope of the following claims.

What is claimed is:

1. A method comprising:
delivering, via a stimulation electrode, electrical stimulation as an initial therapy to a patient according to a set of initial therapy parameters;
sensing, via a sensing electrode and in response to the delivery of the initial therapy, a first electrically evoked compound action potential (eECAP) signal, wherein the first sensed eECAP signal is an eECAP baseline;
delivering, via the stimulation electrode, electrical stimulation as a candidate therapy to the patient according to a set of candidate therapy parameters different from the set of initial therapy parameters;
sensing, via the sensing electrode and in response to the delivery of the candidate therapy, a second eECAP signal;
classifying, via a processor, the sensed second eECAP signal generated in response to the delivery of the candidate therapy relative to the eECAP baseline;
determining a power consumption of the candidate therapy relative to the initial therapy; and
selecting, by the processor and based on the classification of the sensed second eECAP relative to the eECAP baseline and the power consumption of the candidate therapy relative to the initial therapy, one of the initial therapy or the candidate therapy for subsequent electrical stimulation.

2. The method of claim 1, wherein classifying the second sensed eECAP signal comprises classifying the sensed second eECAP signal based on at least one parameter directly measured from or derived from the second sensed eECAP signal.

3. The method of claim 2, wherein classifying the sensed second eECAP signal based on the at least one parameter comprises comparing a value for at least one parameter measured or derived from the sensed second eECAP signal to a value or a range of values for a corresponding parameter measured or derived from the first sensed eECAP signal.

4. The method of claim 2, wherein the at least one parameter measured or derived from the second sensed eECAP signal comprises a measure of fiber latency in the second sensed eECAP signal.

5. The method of claim 2, wherein the at least one parameter measured or derived from the second sensed eECAP signal comprises a measure of a time when masking occurs for a portion of the second sensed eECAP signal attributed to a specific nerve fiber type.

6. The method of claim 2, wherein the at least one parameter measured or derived from the second sensed eECAP signal comprises a measurement of the width of the second sensed eECAP signal.

7. The method of claim 2, wherein the at least one parameter measured or derived from the second sensed eECAP signal comprises a difference value between the fiber latency for a first nerve fiber type with respect the fiber latency for a second nerve fiber type that is a different nerve fiber type than the first nerve fiber type.

8. The method of claim 1, further comprising determining, by the processor, whether to adjust one or more of the set of candidate therapy parameters based on the classification of the second sensed eECAP signal.

9. The method of claim 1, where classifying the second sensed eECAP signal relative to the eECAP baseline comprises determining whether the second sensed eECAP signal is equivalent to the eECAP baseline.

10. The method of claim 1, wherein sensing the second eECAP signal comprises:
at a predetermined time interval following cessation of the application of the candidate therapy, delivering, via the stimulation electrode, an electrical stimulation pulse configured to evoke the second eECAP signal; and
sensing, via the sensing electrode, the second eECAP signal in response to the delivery of the electrical stimulation pulse.

11. The method of claim 1,
wherein sensing the first eECAP signal in response to the delivery of the initial therapy comprises:
at a first predetermined time interval following cessation of the application of the initial therapy, delivering, via the stimulation electrode, a first electrical stimulation pulse configured to evoke the first eECAP signal; and
sensing, via the sensing electrode, the first eECAP signal in response to the delivery of the first electrical stimulation pulse,
wherein sensing the second eECAP signal in response to the delivery of the candidate therapy comprises:
at a second predetermined time interval following cessation of the application of the candidate therapy, delivering, via the stimulation electrode, a second electrical stimulation pulse configured to evoke the second eECAP signal; and sensing, via the sensing electrode, the second eECAP signal in response to the delivery of the second electrical stimulation pulse, and wherein the first predetermined time interval and the second predetermined time interval are substantially the same.

12. The method of claim 1, wherein the eECAP baseline comprises a first plurality of amplitude peaks, each amplitude peak of the first plurality of amplitude peaks occurring after cessation of delivery of the initial therapy and corresponding to an eECAP response of the patient to a stimulation pulse delivered to evoke the eECAP response, wherein the second eECAP signal comprises a second plurality of amplitude peaks, each amplitude peak of the second plurality of amplitude peaks occurring after cessation of delivery of the candidate therapy and corresponding to an eECAP response of the patient to a stimulation pulse delivered to evoke the eECAP response, and wherein classifying the sensed second eECAP signal generated in response to the delivery of the candidate therapy relative to the eECAP baseline comprises comparing the first plurality of amplitude peaks to the second plurality of amplitude peaks.

13. The method of claim 1, further comprising delivering, by the processor and via stimulation electrode, electrical stimulation as the selected one of the initial therapy or the candidate therapy.

14. The method of claim 1, wherein the stimulation electrode is located in proximity to a dorsal column of a patient.

15. The method of claim 1, wherein determining the power consumption of the candidate therapy relative to the initial therapy comprises comparing a predetermined power consumption of the candidate therapy to a predetermined power consumption of the initial therapy.

16. A system comprising:
a stimulation generator configured to deliver electrical stimulation therapy via one or more electrodes; and
a processor configured to:
control the stimulation generator to deliver, via the one or more electrodes, electrical stimulation as an initial therapy to a patient according to a set of initial therapy parameters;
sense, via the one or more electrodes and in response to the delivery of the initial therapy, a first electrically evoked compound action potential (eECAP) signal, wherein the first sensed eECAP signal is an eECAP baseline;
control the stimulation generator to deliver, via the one or more electrodes, electrical stimulation as a candidate therapy to the patient according to a set of candidate therapy parameters different from the set of initial therapy parameters,
sense, via the one or more electrodes and in response to the delivery of the candidate therapy, a second eECAP signal,
classify the second sensed eECAP signal generated in response to the delivery of the candidate therapy relative to the eECAP baseline;
determine a power consumption of the candidate therapy relative to the initial therapy; and
select, based on the classification of the sensed second eECAP relative to the eECAP baseline and the power consumption of the candidate therapy relative to the initial therapy, one of the initial therapy or the candidate therapy for subsequent electrical stimulation.

17. The system of claim 16,
wherein a plurality of sets of stimulation therapy parameters comprise the set of initial therapy parameters and the set of candidate therapy parameters,
wherein the system further comprises a memory configured to store the plurality of sets of stimulation parameters, and
wherein the processor is configured to:
generate the candidate set of therapy parameters, the candidate set including one or more stimulation parameters in association with a change in posture state of the patient; and
store the candidate set of stimulation parameters in the memory.

18. The system of claim 16, wherein the processor is further configured to:
compare one or more parameters of the second sensed eECAP to one or more corresponding parameters of the eECAP baseline; and
adjust at least one of the parameters of the set of candidate therapy parameters based on the comparison to obtain a set of adjusted therapy parameters;
control the stimulation generator to deliver electrical stimulation therapy according to the set of adjusted therapy parameters.

19. The system of claim 16, wherein, to sense the second eECAP signal generated in response to the delivery of the candidate therapy, the processor is further configured to:
at a predetermined time interval following cessation of the application of the candidate therapy, deliver an electrical stimulation pulse configured to evoke the second eECAP signal; and
sense the second eECAP signal in response to the delivery of the electrical stimulation pulse.

20. The system of claim 16, further comprising a memory configure to store the set of candidate therapy parameters including at least one adjusted stimulation parameter.

21. The system of claim 16, wherein to sense the second eECAP signal via the one or more electrodes, the processor is configured to sense the second eECAP signal via one or more electrodes located at a distance from a targeted stimulation nerve site of the patient.

22. A system comprising:
one or more electrodes;
a stimulation generator configured to deliver electrical stimulation therapy via the one or more electrodes; and
a processor configured to:
control the stimulation generator to deliver, via the one or more electrodes, electrical stimulation as an initial therapy to a patient according to a set of initial therapy parameters;
sense, via the one or more electrodes and in response to the delivery of the initial therapy, a first electrically evoked compound action potential (eECAP) signal, wherein the first sensed eECAP signal is an eECAP baseline;
control the stimulation generator to deliver, via the one or more electrodes, electrical stimulation as a candidate therapy to the patient according to a set of candidate therapy parameters different from the set of initial therapy parameters;

sense, via the one or more electrodes and in response to the delivery of the candidate therapy, a second eECAP signal;

classify the second sensed eECAP signal generated in response to the delivery of the candidate therapy relative to the eECAP baseline;

determine a power consumption of the candidate therapy relative to the initial therapy;

adjust at least one stimulation parameter of the set of candidate therapy parameters based on the classification of the sensed second eECAP relative to the eECAP baseline and the power consumption of the candidate therapy relative to the initial therapy; and control the stimulation generator to deliver electrical stimulation to the patient according to the at least one adjusted stimulation parameter of the set of candidate therapy parameters.

23. The system of claim 22, further comprising a posture state module configured to detect a posture state of a patient, wherein the processor is further configured to detect a change in a patient posture state from a first posture state to a second posture state, and wherein sensing the second eECAP signal generated in response to the delivery of the candidate therapy comprises sensing, in response to detecting the change in the patient posture state from the first posture state to the second posture state, the second eECAP signal generated in response to the delivery of the candidate therapy.

24. The system of claim 23, wherein:

the stimulation generator is further configured to deliver electrical stimulation according to a set of therapy parameters associated with the second posture state; and the processor is further configured to:

sense a third eECAP signal generated in response to the delivery of the electrical stimulation according to the set of therapy parameters associated with the second posture state; and adjust at least one stimulation parameter of the set of therapy parameters associated with the second posture state based on the third sensed eECAP generated in response to application of the set of stimulation therapy parameters associated with the second posture state.

* * * * *